(12) United States Patent
Bowman et al.

(10) Patent No.: US 10,017,510 B2
(45) Date of Patent: *Jul. 10, 2018

(54) THIOL-X CLICK FOLDAMERS FOR POLYMER AFFINITY AND CATALYSIS LIBRARIES

(71) Applicant: THE REGENTS OF THE UNIVERSITY OF COLORADO, A BODY CORPORATE, Denver, CO (US)

(72) Inventors: Christopher N. Bowman, Boulder, CO (US); Christopher J. Kloxin, Newark, DE (US); Weixian Xi, Boulder, CO (US); Tao Gong, Denver, CO (US); Sankha Pattanayak, Denver, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/116,978

(22) PCT Filed: Feb. 6, 2015

(86) PCT No.: PCT/US2015/014844
§ 371 (c)(1),
(2) Date: Aug. 5, 2016

(87) PCT Pub. No.: WO2015/120290
PCT Pub. Date: Aug. 13, 2015

(65) Prior Publication Data
US 2017/0015667 A1    Jan. 19, 2017

Related U.S. Application Data

(60) Provisional application No. 61/936,628, filed on Feb. 6, 2014.

(51) Int. Cl.
| | | |
|---|---|---|
| *C07D 473/34* | (2006.01) | |
| *C07D 239/47* | (2006.01) | |
| *C07D 239/54* | (2006.01) | |
| *C07D 473/18* | (2006.01) | |
| *C12Q 1/68* | (2018.01) | |

(Continued)

(52) U.S. Cl.
CPC ......... *C07D 473/34* (2013.01); *C07D 239/47* (2013.01); *C07D 239/54* (2013.01); *C07D 473/18* (2013.01); *C12N 15/1048* (2013.01); *C12N 15/1093* (2013.01); *C12Q 1/6802* (2013.01); *C12Q 1/6876* (2013.01)

(58) Field of Classification Search
CPC .. C07D 473/34; C07D 239/47; C07D 239/54; C07D 473/18; C12N 15/1093; C12N 15/1048; C12Q 1/6802; C12Q 1/6876
See application file for complete search history.

(56) References Cited

U.S. PATENT DOCUMENTS

| 6,075,143 A | 6/2000 | Breipohl et al. |
|---|---|---|
| 2009/0124534 A1 | 5/2009 | Reineke |

(Continued)

FOREIGN PATENT DOCUMENTS

| CA | 2078256 A1 | 3/1994 |
|---|---|---|
| JP | 258222 A | 10/1995 |

(Continued)

OTHER PUBLICATIONS

Xi, W., et al.; Clickable Nucleic Acids, presented at 245$^{th}$ ACS Annual Conference, Apr. 11, 2013.*
U.S. Appl. No. 14/388,748, filed Sep. 26, 2014, First Named Inventor Christopher N. Bowman (264 pages).
Japanese Office Action issued in JP Patent Application No. 2015-503259 dated Oct. 18, 2016, with English translation of same (16 pages).
Hoyle et al., "Thiol-click chemistry: a multifaceted toolbox for small molecule and polymer synthesis", Chem Soc Rev. Apr. 2010;39(4):1355-87. doi: 10.1039/13901979k. Epub Feb. 9, 2010.
Zhang et al., "Synthesis and hybridization property of an oligonucleotide containing a 3-thioformacetal linked pentathymidylate", Bioorg Med Chem Lett. Feb. 8, 1999;9(3):319-22.

(Continued)

*Primary Examiner* — Robert Jones, Jr.
(74) *Attorney, Agent, or Firm* — Fisherbroyles, LLP; Jason M. Pass

(57) ABSTRACT

Click thiol-X monomers and polymers containing such monomers are disclosed. The clickable sequence controllable monomers include an optionally protected thiol moiety; an optionally protected Michael acceptor moiety; a primary functional side chain and one ore more secondary functional side chains. A clickable sequence controllable monomer, can have the structure:

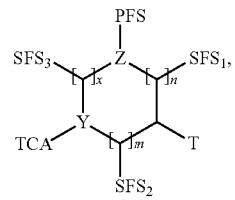

wherein independently Y and Z are atoms having a valence electrons of 3 or more; n is a integer from 0-10; m is a integer from 0-10; x is a integer from 0-10; PFS is a functional group SFSi; SFS2; and SFS3 are independently a combination of hydrogen, hydroxyl, aromatic, amine, carboxyl, and carbonyls, optionally substituted to form hydrophilic, hydrophobic, amphiphilic, or charged (positive or negative or both) side chains; T is an optionally protected thiol; and TCA is an optionally protected thiol-click acceptor. Methods of using such polymers are also disclosed.

20 Claims, 10 Drawing Sheets

(51) Int. Cl.
*C12Q 1/6876* (2018.01)
*C12N 15/10* (2006.01)

(56) References Cited

U.S. PATENT DOCUMENTS

| 2011/0077407 | A1 | 3/2011 | David et al. |
| 2011/0129921 | A1 | 6/2011 | Johnson et al. |
| 2011/0171448 | A1 | 7/2011 | Tang et al. |
| 2012/0071641 | A1 | 3/2012 | Manoharan et al. |

FOREIGN PATENT DOCUMENTS

| WO | 1989012060 | A1 | 12/1989 |
| WO | 1995031470 | A2 | 11/1995 |
| WO | 199604295 | A1 | 2/1996 |
| WO | 2010048549 | A2 | 4/2010 |
| WO | 2013148165 | A1 | 10/2013 |

OTHER PUBLICATIONS

Konkolewicz et al., "Hyperbranched polymers by thiol-yne chemistry: from small molecules to functional polymers", J Am Chem Soc. Dec. 23, 2009;131(50):18075-7. doi: 10.1021/ja908206a.
English Translation of First Office Action dated Sep. 6, 2015, in Chinese Patent Application No. CN 201380024075.7 (8 pages).
English Translation of Second Office Action dated Jun. 20, 2016, in Chinese Patent Application No. CN 201380024075.7 (9 pages).
Communication Pursuant to Rules 70(2) and 70a(2) EPC dated Jun. 17, 2016 in European Patent Application No. 13767244.0 (1 page).
Extended European Search Report dated May 31, 2016 in European Patent Application No. 13767244.0 (9 pages).
Dose et al., "Convergent synthesis of peptide nucleic acids by native chemical ligation", Org Lett. Sep. 29, 2005;7 (20):4365-8.
Gogoi et al., "Sugar-thioacetamide backbone in oligodeoxyribonucleosides for specific recognition of nucleic acids", Chem Commun (Camb). Jun. 14, 2006;(22):2373-5. Epub Apr. 25, 2006.
Pensato et al., "New Synthetic Rout to [gamma]-Mercaptomethyl PNA Monomers", Synthetic Communications, vol. 38, No. 15, Jul. 24, 2008 (Jul. 24, 2008), pp. 2499-2506, XP055272645, Philadelphia, PA; US ISSN: 0039-79111 DOI: 10.1088/00397910802219122.
Scheibe et al., "DNA-programmed spatial screening of carbohydrate-lectin interactions", Chemical Science, vol. 2., No. 4, Jan. 1, 2011 (Jan. 1, 2011) p. 770, XP055272631, United Kingdom, ISSN: 2041-6520, DOI: 10.1039/c0c00565g.
Mourtas et al., "S-4 Methoxytrityl Mercapto Acids: Synthesis and Application," Tetrahedron Letters, vol. 42, Issue 39, Sep. 24, 2001, pp. 6965-6967.
PubChem Record CID 2245987, URL: http://pubchem.ncbi.nlm.nih.gov/summary/summary.cgi?cid=2245987, Create Date: Jul. 15, 2005, Accessed: Apr. 13, 2013, pp. 1-3.
PubChem Record CID 201366, URL: http://pubchem.ncbi.nlm.nih.gov/summary/summary.cgi?cid=201366, Create Date: Aug. 9, 2005, Accessed: Apr. 13, 2013, pp. 1-3.
PubChem Record CID 5232652, URL: http://pubchem.ncbi.nlm.nih.gov/summary/summary.cgi?cid=5232652, Create Date: Oct. 7, 2005, Accessed: Apr. 13, 2013, pp. 1-3.
International Search Report issued on Jun. 4, 2015 in PCT/US2015/014844, Applicant The Regents of The University of Colorado, A Body Corporate (3 pages).
Written Opinion dated Jun. 4, 2015 in PCT/US2015/014844, Applicant The Regents of The University of Colorado, A Body Corporate (4 pages).
Chinese Office Action issued in CN Patent Application No. 201380024075.7 dated Feb. 14, 2017, with English translation of same (13 pages).
EP 12 746 630.1 Thiol-X Click Foldamers for Polymer Affinity and Catalysis Libraries; Extended European Search Report dated Jun. 8, 2017, for corresponding European Application.
U.S. Appl. No. 14/388,748 Click Nucleic Acids Notice of Allowance dated Sep. 13, 2017.
JP 2015-503259 Click Nucleic Acids; Decision to Grant dated Sep. 5, 2017. Allowed Claims attached herewith.
CN 201380024075.7 Click Nucleic Acids; Office Action dated Feb. 14, 2017.
EP Communication pursuant to Article 94(3) EPC dated Apr. 23, 2018 issued in EP 13767244.0 (7 pages).

* cited by examiner

FIG. 8
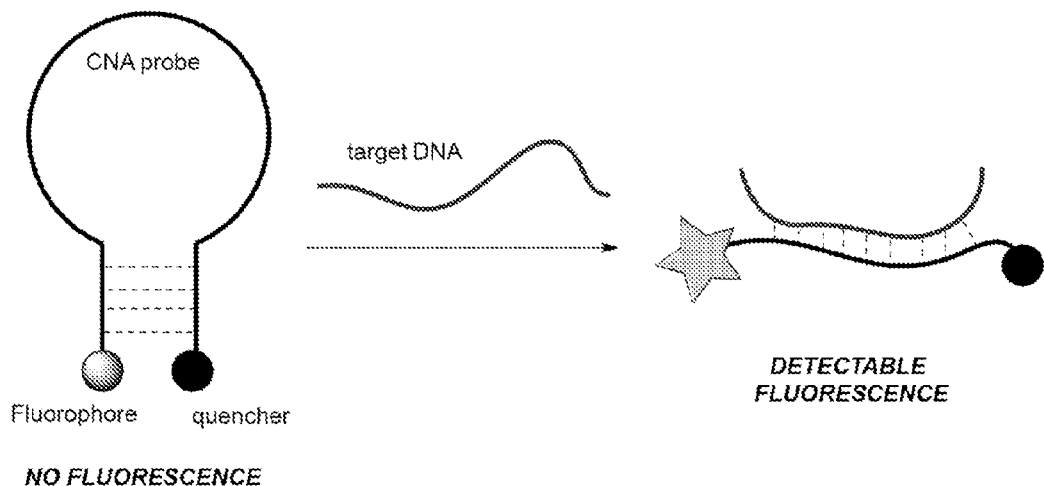
FIG. 9A
FIG. 9B
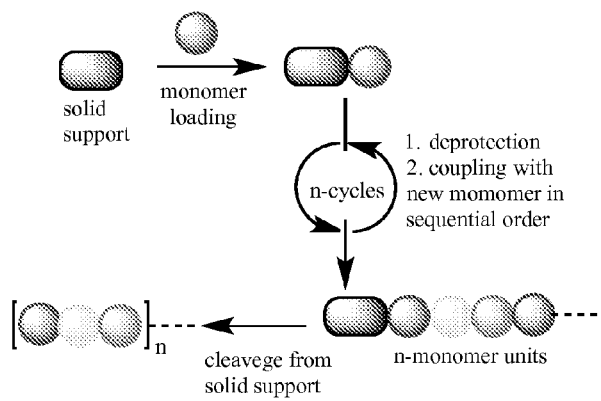
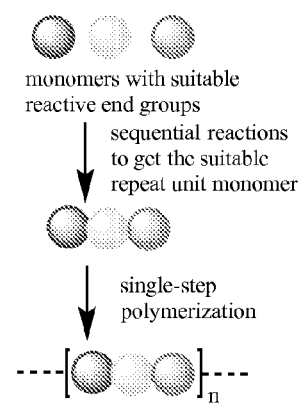

THIOL-X CLICK FOLDAMERS FOR POLYMER AFFINITY AND CATALYSIS LIBRARIES

CROSS-REFERENCE TO RELATED APPLICATION

The present invention is filed under 35 U.S.C. § 371 as the U.S. national phase of International Application No. PCT/US2015/014844, filed Feb. 6, 2015, which designated the U.S. and claims the priority benefit of U.S. Provisional Application No. 61/936,628, filed on Feb. 6, 2014, each of which is incorporated herein by reference in its entirety.

STATEMENT OF GOVERNMENT SUPPORT

This invention was made with government support under grant number R21 CA174479 awarded by the National Institutes of Health. The government has certain rights in the invention.

FIELD

This disclosure relates to synthetic polymers, and specifically to thiol-X polymers and their use as affinity and catalysis reagents.

BACKGROUND

Nucleic acid-based molecules, such as DNA, RNA, and PNA (peptide nucleic acids), have continued to find ever-increasing levels of implementation and exciting applications in biology and biomedical systems, whether for gene knockout, as aptamers, for drug delivery and targeting, in biodetection, and in many other areas. While these molecules and approaches are highly valuable in numerous arenas, they are limited in one capacity or another by the chemistry used to assemble these structures. DNA and RNA are enzymatically cleavable, expensive, potentially immunogenic and with limited chemical versatility. In contrast, PNAs are difficult to form, using inefficient chemistries that require large stoichiometric excesses and limit yields, particularly of high molecular weight compounds. Further, they are also enzymatically cleavable though they do have a much greater level of structural variability that is possible. Thus, it would beneficial to have additional reagents that can be made en mass in a cost effective manner. This disclosure meets those needs.

SUMMARY

Disclosed are clickable sequence controllable monomers. In some embodiments the clickable sequence controllable monomers include an optionally protected thiol moiety; an optionally protected Michael acceptor moiety; a primary functional side chain such as nucleobase (NB), modified nucleobase acetic acid, lipophilic and polar acid, sugar, cationic and anioic groups, amino acids; and a secondary functional side chain.

In some embodiments, a clickable sequence controllable monomer, has structure:

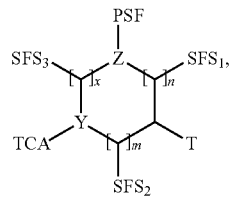

wherein independently Y and Z are atoms having a valence electron of 3 or more; n is a integer from 0-10; m is a integer from 0-10; x is a integer from 0-10; PFS (primary functional side chain) is a functional group, such as optionally protected nucleobases (A, T, G, C, or U), modified nucleobase acetic acids, amino acids (α-, β-, γ-, and δ), lipophilic and polar acids, sugars, cationic and anionic group, etc; $SFS_1$; $SFS_2$; and $SFS_3$ (secondary functional side chain 1, 2, 3) are independently a combination of hydrogen, hydroxyl, aromatic, amine, carboxyl, and carbonyls, optionally substituted to form hydrophilic, hydrophobic, amphiphilic, or charged (positive or negative or both) side chains; T is an optionally protected thiol; and TCA is an optionally protected thiol-click acceptor.

In some embodiments, a clickable sequence controllable monomer, has structure:

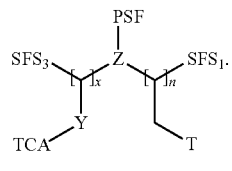

Also disclosed are thiol-X polymers that include a disclosed clickable sequence controllable monomer and/or a click nucleic acid. Such polymers are end linked between the thiol moiety and the terminal end of the thiol-click acceptor moiety. In some examples, the thiol-X molecules are conjugated to one or more additional molecules, such as effector molecules. In some embodiments, for example as a therapeutic, the thio-ether nucleic acid polymer is provided as a composition, such as a composition that includes a pharmaceutically acceptable carrier. Methods of using such polymers, for example in place of DNA, RNA, morpholino nucleic acids (MNA) and/or synthetic nucleic acid mimetics, such as PNAs, are also contemplated.

The foregoing and other, features, and advantages of this disclosure will become more apparent from the following detailed description, which proceeds with reference to the accompanying figures.

BRIEF DESCRIPTION OF THE DRAWINGS

FIG. 8 is a schematic showing the mechanism of action for CNA molecular beacons.

FIGS. 9A and 9B are schematics showing the difference between conventional stepwise synthesis and one-step polymerization strategies. FIG. 9A shows stepwise synthesis needs several deprotection and coupling steps; FIG. 9B shows a polymerization strategy needing a one-step polymerization reaction of suitable monomers.

DETAILED DESCRIPTION

I. Summary of Terms

Figure 1:
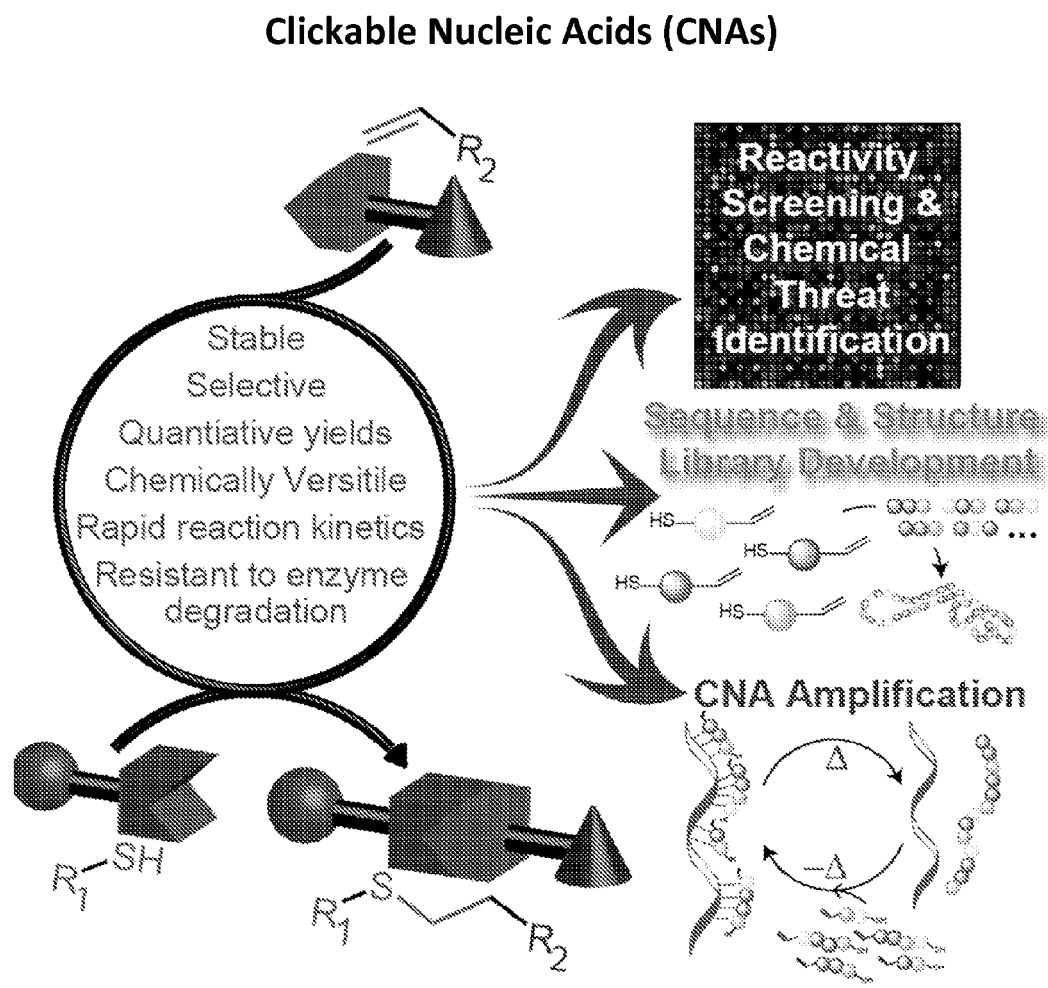
FIG. 1 is a schematic showing that the attributes of the thiol-X click reaction mechanism enable a wide array of applications.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: A Comprehensive Desk Reference, published by VCH Publishers, Inc., 1995 (ISBN 9780471185710). Definitions of common terms in chemistry may be found in Richard J. Lewis, Sr. (ed.), Hawley's Condensed Chemical Dictionary, published by John Wiley & Sons, Inc., 1997 (ISBN 0-471-29205-2).

To facilitate review of the various embodiments of the disclosure, the following explanations of specific terms are provided:

Administration: To provide or give a subject an agent, such as thiol-X polymer disclosed herein, by any effective route. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes.

Animal: A living multicellular vertebrate organism, a category that includes, for example, mammals. A "mammal" includes both human and non-human mammals, such as mice. The term "subject" includes both human and animal subjects, such as mice. In some examples, a subject is a patient.

Antisense compound: Refers to an oligomeric compound that is at least partially complementary to the region of a target nucleic acid molecule (for example a CNA having nucleobases that are at least partially complementary) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression.

Nonlimiting examples of antisense compounds include primers, probes, antisense oligonucleotides, and CNAs comprising the same.

Alkoxy: A —$OZ_1$ radical, where $Z_1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, and the like. A related term is "aryloxy" where $Z_1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

Alkyne moiety: A hydrocarbon that has a triple bond between two carbon atoms, with the formula —$CCR_1$, where $R_1$ can be independently hydrogen, hydrocarbyl, substituted hydrocarbyl, substituted heterocyclo, alkyl, substituted alkyl, acyl, —C(O)R, —C(O)OR, or —C(O)$NR_aR_b$, aryl or substituted aryl or heterocyclic ring.

Alkyl: A linear, branched, or cyclic, hydrocarbon chain, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. "Branched" refers to an alkyl group in which an alkyl group, such as methyl, ethyl or propyl, is attached to a linear alkyl chain.

Amino: The group —NZ$_1$Z$_2$, where each of Z$_1$ and Z$_2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

Aptamer: Small nucleic acid and molecules that bind a specific target molecule, such as a target biomolecule, for example an analyte, such as a target analyte. In some examples, an aptamer is a CNA molecule. Aptamers are known in the art and have been obtained through a combinatorial selection process called systematic evolution of ligands by exponential enrichment (SELEX) (see for example Ellington et al., *Nature* 1990, 346, 818-822; Tuerk and Gold *Science* 1990, 249, 505-510; Liu et al., *Chem. Rev.* 2009, 109, 1948-1998; Shamah et al., *Acc. Chem. Res.* 2008, 41, 130-138; Famulok, et al., *Chem. Rev.* 2007, 107, 3715-3743; Manimala et al., *Recent Dev. Nucleic Acids Res.* 2004, 1, 207-231; Famulok et al., *Acc. Chem. Res.* 2000, 33, 591-599; Hesselberth, et al., *Rev. Mol. Biotech.* 2000, 74, 15-25; Wilson et al., *Annu. Rev. Biochem.* 1999, 68, 611-647; Morris et al., *Proc. Natl. Acad. Sci. U.S.A.* 1998, 95, 2902-2907). In such a process, DNA or RNA molecules that are capable of binding a target molecule of interest are selected from a nucleic acid library consisting of $10^{14}$-$10^{15}$ different sequences through iterative steps of selection, amplification and mutation. Many aptamers that are specific to a wide range of targets from small organic molecules such as adenosine, to proteins such as thrombin, and even viruses and cells (Liu et al., *Chem. Rev.* 2009, 109, 1948-1998; Lee et al., *Nucleic Acids Res.* 2004, 32, D95-D100; Navani and Li, *Curr. Opin. Chem. Biol.* 2006, 10, 272-281; Song et al., *TrAC, Trends Anal. Chem.* 2008, 27, 108-117). The affinity of the aptamers towards their targets can rival that of antibodies, with dissociation constants in as low as the picomolar range (Morris et al., *Proc. Natl. Acad. Sci. U.S.A.* 1998, 95, 2902-2907; Green et al., *Biochemistry* 1996, 35, 14413-14424).

Aryl: An aromatic substituent, which can be a single aromatic ring or multiple aromatic rings, which are fused together, linked covalently, or linked to a common group such as a methylene or ethylene moiety. The common linking group can also be a carbonyl as in benzophenone or oxygen as in diphenylether or nitrogen in diphenylamine. The aromatic ring(s) can include phenyl, naphthyl, biphenyl, diphenylether, diphenylamine and benzophenone among others. In particular embodiments, the term "aryl" means a cyclic aromatic comprising about 5 to about 10 carbon atoms, including 5- and 6-membered hydrocarbon and heterocyclic aromatic rings.

The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

Contacting: Placement in direct physical association including both in solid or liquid form, for example contacting a sample with a disclosed polymer. Contacting can occur in vitro, for example in a diagnostic assay, or in vivo, for example by administering an agent to a subject.

Covalent bond: An interatomic bond between two atoms, characterized by the sharing of one or more pairs of electrons by the atoms. The terms "covalently bound" or "covalently linked" refer to making two separate molecules into one contiguous molecule, for example a nucleobase and a CNA backbone, or a CNA molecule and a second molecule, such as an effector molecule.

Detectable label: A detectable molecule (also known as a label) that is conjugated directly or indirectly to a second molecule, such as a disclosed polymer molecule, to facilitate detection of the second molecule. For example, the detectable marker can be capable of detection by diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Various methods of labeling polypeptides are known in the art and may be used.

Detect: To determine if an agent (such as a signal or particular CNA probe, or molecule bound be such a CNA probe) is present or absent. In some examples, this can further include quantification.

Effector molecule: A molecule intended to have or produce a desired effect, such as a therapeutic effect, detection, or other physical effect, such as but not limited to localization of the effector molecule. Effector molecules include such molecules as polypeptides, radioisotopes and small molecules (for example drugs) and labels.

Electron withdrawing group: Any substituent that draws electrons away from a vinyl bond. Exemplary electron withdrawing groups include hydroxy, alkoxy, mercapto, halogens, carbonyls, sulfonyls, nitrile, quaternary amines, nitro, trihalomethyl, imine, amidine, oxime, thioketone, thioester, or thioamide.

Epoxide: A cyclic ether with three ring atoms, in which two of the atoms are carbon and the remaining atom is oxygen bonded to the two carbons.

Halide or halo: An atom from the group of Br, Cl, I and F.

Heteroatom: An atom other than carbon. In some embodiments, the heteroatoms are selected from the group consisting of N, O, P, S, Si, B, Ge, Sn, and Se.

Heterocyclo or heterocyclic: An optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxyl, protected hydroxyl, acyl, acyloxy, alkoxy, alkenoxy, alkynoxy, aryloxy, halogen, amido, amino, nitro, cyano, thiol, ketals, acetals, esters and ethers.

Hybridization: Oligonucleotides and their analogs, such as CNAs. hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or t'wo distinct regions of the same nucleic acid sequence.

"Specifically hybridizable" and "specifically complementary" are terms that indicate a sufficient degree of complementarity such that stable and specific binding occurs between the oligonucleotide (or it's analog, such as a CNA) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency.

Hydrocarbon or hydrocarbyl: Organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, as alkaryl, alkenaryl, and alkynaryl.

"Substituted hydrocarbyl", are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substitutents include halogen, heterocyclo, alkoxy, alkenoxy, alkynoxy, aryloxy, hydroxyl, protected hydroxy, keto, acyl, acyloxy, nitro, amino, amido, nitro, cyano, thiol, ketals, acetals, esters and ethers.

Label: A detectable compound or composition, which can be conjugated directly or indirectly to another molecule, such as a disclosed polymer, to facilitate detection of that molecule, or a molecule to which a disclosed polymer binds. Specific, non-limiting examples of labels include fluorescent tags, enzymes, and radioactive isotopes. Examples of labels include, but are not limited to, the following: radioisotopes or radionuclides (such as $^{35}S$ or $^{131}I$), fluorescent labels (such as fluoroscein istothiocyanate (FITC), rhodamine, lanthanide phosphors, cyanine dyes, fluorescent proteins, such as GFP), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms, such as linkers, of various lengths, for example to reduce potential steric hindrance.

Linker: A compound or moiety that acts as a molecular bridge to operably link two different molecules, wherein one portion of the linker is operably linked to a first molecule and wherein another portion of the linker is operably linked to a second molecule. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens and the like.

Mimetic: A molecule (such as an organic chemical compound) that mimics the activity and/or structure of an agent, such as the activity of a nucleic acid, such as RNA and DNA. In one embodiment, a mimetic of a nucleic acid is a click nucleic acid (CAN).

Nucleobase: A nucleotide includes a nitrogen-containing base, which can be attached to a polymer backbone, such as a deoxyribonucleic, ribonucleic or thio-ether backbone among others.

The major nucleobases are adenosine (A), guanosine (G), cytidine (C), thymidine (T) uridine (U).

Nucleobases also include modified bases, for example as described in U.S. Pat. No. 5,866,336. Examples of modified base moieties include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine amongst others.

Probe: A probe comprises an isolated nucleic acid or disclosed nucleic acid memetic capable of hybridizing to a target nucleic acid, and a detectable label or reporter molecule can be attached to a nucleic acid molecule. Typical labels include radioactive isotopes, enzyme substrates, cofactors, ligands, chemiluminescent or fluorescent agents, haptens, and enzymes.

Probes are generally at least 6 bases in length, such as at least 6, at least 7, at least 8, at least 9, least 10, at least 11, at least 12, at least 13, at least 14, at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 70, at least 80, at least 90, at least 100, at least 120, at least 140, at least 160, at least 180, at least 200, at least 250, at least 300, at least 350, at least 400, at least 450, at least 500, or more contiguous bases complementary to the target nucleic acid molecule, such as 6-500 nucleotides, 20-400 nucleotides, 100-250 nucleotides, 20-40 nucleotides, or 20-30 nucleotides. In some examples a probe is molecular beacon.

Pharmaceutically acceptable carriers: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of the nanoparticles disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Sample: A sample, such as a biological sample, is obtained from an animal subject, such as a human subject. As used herein, biological samples include all clinical samples, including, but not limited to, cells, tissues, and bodily fluids, such as: blood; derivatives and fractions of blood, tissue biopsy (including shave, punch, or excision biopsy of atypical or suspicious nevi) including tissues that are, for example, unfixed, frozen, fixed in formalin and/or embedded in paraffin. In some examples, a sample is one obtained from a subject having, suspected of having, or who has had, for example is diagnosed with melanoma, such as metastatic melanoma.

A polymer is a molecule with repeating general structural units (e.g., monomers) formed via a chemical reaction, e.g., polymerization.

Sequence identity/similarity: The identity/similarity between two or more nucleic acid sequences, nucleic acid sequEnce and a CNA sequences or two or more CNA sequences, is expressed in terms of the identity or similarity between the sequences. Sequence identity can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. One indication that two nucleic acid molecules and/or CNAs are closely related is that the two molecules hybridize to each other under stringent conditions.

Synthetic nucleic acids: Polymer molecules that include those constructed by joining nucleic acid containing molecules, for example nucleic acid molecules that are chemically or by other means synthesized or amplified, including those that are chemically or otherwise modified but can base pair with naturally occurring nucleic acid molecules, or with other synthetic nucleic acids. In one example, a synthetic nucleic acid id a CNA.

Click nucleic acids or CNAs, (molecule or sequence): A DNA and/or RNA mimetic polymer having a thio-ether backbone in place of the phosphate backbone typically found in DNA or RNA. The CNA can be double stranded (ds) or single stranded (ss) or even more, such as a triple helix. Where single stranded, the nucleic acid can be the sense strand or the antisense strand. CNA can include natural nucleobases (such as A, T/U, C, and G), and can include analogs of natural nucleobases, such as labeled nucleotides.

Thiol or thiol moiety or group: A carbon-bonded sulfhydryl (—C—SH or R—SH) group. In some examples, a thiol moiety is a protected thiol. Examples of thiol protecting groups are known in the art.

Thiol click chemistry: A reaction between a thiol moiety and thiol-click accepting group, such as a vinyl, alkyne, halide, isocyanate or epoxy moiety, achieved by one of many reaction mechanisms. Examples of thiol click chemistry reactions can be found in Hoyle et al. "Thiol-click chemistry: a multifaceted toolbox for small molecule and polymer synthesis", *Chemical Society Reviews* 39 (4) 1355-1387 (2010), which is specifically incorporated herein in its entirety.

Thiol-click acceptor: A thiol-click acceptor is any chemical moiety that readily reacts with thiol, which may or may not contain a protecting group, to produce a thioether. Examples of such moieties are vinyl, vinyl ether, allyl ether, norbornene, vinyl sulfone, epoxy, acrylate, methacrylate, maleimide, halide any Micheal's reaction acceptor, and alkyl extensions thereof.

Suitable methods and materials for the practice or testing of this disclosure are described below. Such methods and materials are illustrative only and are not intended to be limiting. Other methods and materials similar or equivalent to those described herein can be used.

II. Description of Exemplary Embodiments

A. Introduction

The click reaction paradigm is ideally suited to be the reaction framework for accelerated biomaterials and molecular discovery. The concept of spring-loaded reactions that proceed to high yield, generally in an ambient environment with few if any side reactions and without interactions with other functional groups introduces a level of simplicity and elegance that is critical for novel materials design and enabling in the formation of compound libraries with systematically varying physicochemical structure and enhanced behavior. While these reactions enable an unbounded landscape of potential chemical structures, the underlying motivation for molecular design is to create materials with new and/or improved function.

Nature provides the blueprint for chemical structures that possess extraordinary function, from DNA information storage to enzyme catalysis, while also providing the blueprint and methodology for evolving an optimal structure from a vast array of compounds. While, nature is thus far unsurpassed in its ability to create sequence specific macromolecules that are capable of folding and assembling into many functional structures, they often exhibit poor environmental stability, are susceptible to degradation by a range of enzymes (e.g., nucleases and proteases), are often not scalable, lead to immunogenic responses and have a limited range of chemical versatility within which to optimize binding and catalytic activity. The potential for bioinspired macromolecular analogs that are synthesized utilizing a click reaction scheme is unparalleled and will enable rapid discovery of new functional materials that address these limitations.

Disclosed herein is a methodology of creating synthetic nucleic acid and, amino acid-like polymers that has the potential to augment and possibly sweep aside multiple technologies, from nanoassembly to genetic diagnostics to targeted chemical neutralization and catalysis. In addition, the low cost (e.g., orders of magnitude less than DNA based on completely synthetic, non-biological approaches to production) and phenomenal properties (enzymatic and thermal stability, binding selectivity, and chemical versatility) will be the basis for a novel synthetic nucleic and amino acid macromers will 1) have excellent environmental stability, 2) low immunogenic response, 3) chemical versatility, 4) resistance to nucleases and proteases, and 5) capacity for enhanced complexity in their folding and binding.

Figure 2:
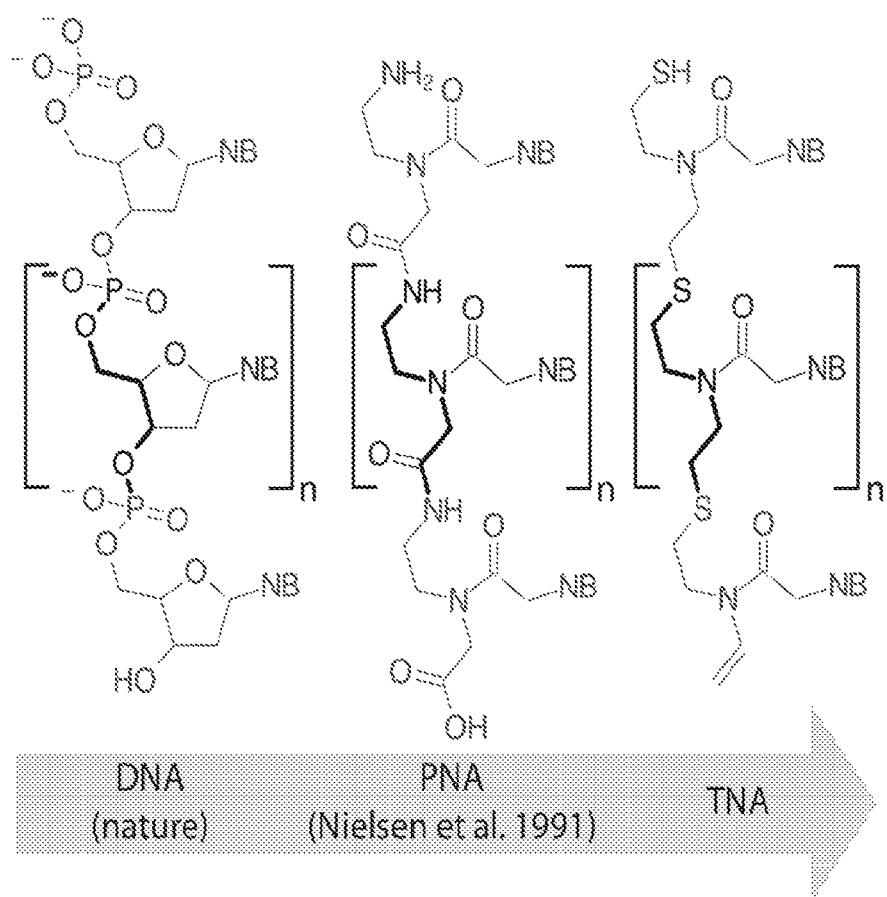
FIG. 2 shows possible structures of the oligonucleotide classes DNA, PNA and CNA. Depicted is the structural evolution of the backbone polymer from the natural biopolymer DNA to artificial biopolymers of PNA and one possible CNA structure. In this example, the CNA backbone is designed to have similar molecular spacing to both PNA and DNA, have a thio-ether backbone formed from the thiol-X click reaction disclosed herein, and have the capacity for hybridization with other oligonucleotides including DNA to induce controlled assembly and biofunctionality.

With reference to FIG. 1 the present disclosure concerns the thiol-X family of click reactions, primarily focused on the thiol-ene and thiol-Michael click reactions to assemble complex, sequence controlled polymers from libraries of monomers, such as click nucleic acids (CNAs) that eliminate the phosphate-sugar backbone of DNA and replace it with a thiol-X based backbone. Disclosed herein is a novel class of biofunctional oligonucleotides, such as clickable nucleic acids or CNAs, that utilize the thiol-X 'click' reaction family to form the desired base sequence in a sequence controlled manner. The CNA structure, illustrated alongside DNA and PNA structures in FIG. 2, as a broad class of materials has several distinct advantages that enhance its significance, particularly, (i) the use of click chemistry (reaction efficiency, scaling, orthogonality, high yield), (ii) the capability to photoinitiate the reaction (spatioselectivity), (iii) the formation of a thioether backbone that enhances the CNA stability (i.e., resistance to hydrolytic or enzymatic degradation), (iv) CNA-DNA binding is more thermally stable than DNA-DNA, (v) more sensitive to nucleobase mismatches, and (vi) the CNA material is several orders of magnitude less expensive than DNA.

The implementation of click chemistry in the production of oligonucleotides has numerous distinct advantages as previously indicated; however, one of the greatest advantages of this approach is the robustness of the monomer structures that can be implemented and the capabilities that are derived from those structural variations. This structural variation, along with the capacity for clicking the monomers together with all the benefits of click chemistry, is the defining feature of this approach. The monomer structural variation possible with CNAs dramatically expands the DNA alphabet from its four bases (five with RNAs) and enables vast, powerful features that are not achievable by either DNA or other synthetic oligonucleotides such as PNAs. In particular, as critical in the development of libraries of foldable, binding materials, CNA monomers have the capacity for chemical structural variations that control charge density, chirality of the units, enable aqueous solubility, dictate the stiffness of the backbone, manipulate the electron transport characteristics, and enable the consideration of non-nuclear bases/interacting moieties.

Broadly, in the expanded CNA alphabet of monomer structures, each monomer contains at least four potentially distinct elements consisting of two independent reactive functional groups, a core linker and the specific nucleobase that will lead to the necessary sequence-specific molecular interactions. In certain embodiments, each of the functional groups used here will be either a thiol or a vinyl group. The vinyl group is selected from those that are capable of undergoing base/nucleophile catalyzed thiol-Michael addition (such as acrylamides or vinyl sulfones) or those that undergo radical-mediated thiol-ene reactions (such as vinyl amine, allyl amine, vinyl ether, etc.). The desired library of compounds is then formed simply by conducting a polymerization of the monomers where the click nature of the reaction guarantees the formation of all random combinations of repeat units.

B. Thiol-X Click Monomers and Polymers

Disclosed are clickable sequence controllable monomers, also referred to herein as thiol-X monomers. In some embodiments, the clickable sequence controllable monomers are thiol-Michael type clickable sequence controllable monomers that include an optionally protected thiol moiety, an optionally protected Michael acceptor moiety, a primary functional side chain, such as nucleobase (NB), modified nucleobase acetic acid, lipophilic and polar acid, sugar, cationic and anioic group, amino acid, and a secondary functional side chain. The clickable sequence controllable monomers, such as clickable nucleic acid monomers, can include a primary functional side chain (PFS) such as nucleobase (NB which in some examples is an A, G, T, U, or C nucleobase). In some embodiments, the disclosed thiol-Michael acceptor is α,β-unsaturated carbonyl compound such as acrylate, acrylamide, vinylsulfone, maleimide, α,β-unsaturated ketone.

In some embodiments, a clickable sequence controllable monomer has structure:

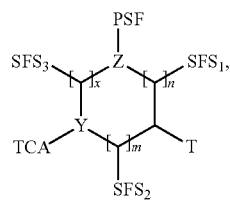

wherein independently Y and Z are atoms having a valence electrons of 3 or more, such as C, N, or B boron, n is a integer from 0-10, such as 0, 1, 2, 3, 4, 5, 6, 7, 8, 9 and/or 10, for example from 1-1, 0-2, 0-3, 0-5, 0-8, 2-10, 1-2, 4-8, 5-10, 2-7, 3-4, and the like, which may include heteroatoms and be independently substituted, for example with aryl, hydroxyl, carbonyl, carboxylic and other acids, amino, alkyl amide, thioether, cyclic, heterocyclic, and alkyl extensions thereof, m is an integer of from 0-10, such as 0, 1, 2, 3, 4, 5, 6, 7, 8, 9 and/or 10, for example from 1-1, 0-2, 0-3, 0-5, 0-8, 2-10, 1-2, 4-8, 5-10, 2-7, 3-4, and the like, which may include heteroatoms and be independently substituted, for example with aryl, hydroxyl, carbonyl, carboxylic and other acids, amino, alkyl amide, thioether, cyclic, heterocyclic, and alkyl extensions thereof, x is a integer from 0-10, such as 0, 1, 2, 3, 4, 5, 6, 7, 8, 9 and/or 10, for example from 1-1, 0-2, 0-3, 0-5, 0-8, 2-10, 1-2, 4-8, 5-10, 2-7, 3-4, and the like, which may include heteroatoms and be independently substituted, for example with aryl, hydroxyl, carbonyl, carboxylic and other acids, amino, alkyl amide, thioether, cyclic, heterocyclic, and alkyl extensions thereof, PFS (primary functional side chain) is a functional group, such as optionally protected nucleobases (A, T, G, C, or U), modified nucleobase acetic acids, amino acids (α-, β-, γ-, and δ), lipophilic and polar acids, sugars, cationic and anionic group, SFS1; SFS2; and SFS3 (secondary functional side chain 1, 2, and 3) are independently a combination of hydrogen, hydroxyl, aromatic, amine, carboxyl, and carbonyls, optionally substituted to form hydrophilic, hydrophobic, amphiphilic, or charged (positive or negative or both) side chains; T is an optionally protected thiol, and TCA is an optionally protected thiol-click acceptor, such as optionally protected vinyl, vinyl ether, allyl ether, norbornene, vinyl sulfone, epoxy, acrylate, methacrylate, maleimide, halide, or other Michael acceptor, such as ketone or nitro group and alkyl extensions thereof.

In certain embodiments a clickable sequence controllable monomer has structure:

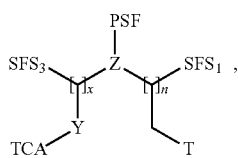

wherein independently Y and Z are atoms having a valence electrons of 3 or more, such, m such as C, N, or B boron, n is a integer from 0-10, such as 0, 1, 2, 3, 4, 5, 6, 7, 8, 9 and/or 10, for example from 1-1, 0-2, 0-3, 0-5, 0-8, 2-10, 1-2, 4-8, 5-10, 2-7, 3-4, and the like, which may include heteroatoms and be independently substituted, for example with aryl, hydroxyl, carbonyl, carboxylic and other acids, amino, alkyl amide, thioether, cyclic, heterocyclic, and alkyl extensions thereof, m is an integer of from 0-10, such as 0, 1, 2, 3, 4, 5, 6, 7, 8, 9 and/or 10, for example from 1-1, 0-2, 0-3, 0-5, 0-8, 2-10, 1-2, 4-8, 5-10, 2-7, 3-4, and the like, which may include heteroatoms and be independently substituted, for example with aryl, hydroxyl, carbonyl, carboxylic and other acids, amino, alkyl amide, thioether, cyclic, heterocyclic, and alkyl extensions thereof, x is a integer from 0-10, such as 0, 1, 2, 3, 4, 5, 6, 7, 8, 9 and/or 10, for example from 1-1, 0-2, 0-3, 0-5, 0-8, 2-10, 1-2, 4-8, 5-10, 2-7, 3-4, and the like, which may include heteroatoms and be independently substituted, for example with aryl, hydroxyl, carbonyl, carboxylic and other acids, amino, alkyl amide, thioether, cyclic, heterocyclic, and alkyl extensions thereof, PFS (primary functional side chain) is a functional group, such as optionally protected nucleobases (A, T, G, C, or U), modified nucleobase acetic acids, amino acids (α-, β-, γ-, and δ), lipophilic and polar acids, sugars, cationic and anionic group, SFS1; and SFS3 (secondary functional side chain 1 and 3) are independently a combination of hydrogen, hydroxyl, aromatic, amine, carboxyl, and carbonyls, optionally substituted to form hydrophilic, hydrophobic, amphiphilic, or charged (positive or negative or both) side chains; T is an optionally protected thiol, and is an optionally protected thiol-click acceptor, such as optionally protected vinyl, vinyl ether, allyl ether, norbornene, vinyl sulfone, epoxy, acrylate, methacrylate, maleimide, halide, or other Michael acceptor, such as ketone or nitro group and alkyl extensions thereof.

In some embodiments, a clickable sequence controllable monomer has no limit of number of atoms in repeat unit inclusive of the optional protected thiol moiety and the terminal carbon. In some embodiments, a clickable sequence controllable monomer has a 3-10, atom repeating unit spacing, such as a 3, 4, 5, 6, 7, 8, 9, 10 or even longer repeating unit spacing, such, 5-9, 5-7-atom repeat unit spacing. In some examples, a clickable sequence controllable monomer has a 6-atom repeat unit inclusive of the thiol moiety and the terminal carbon of the Michael acceptor moiety.

In some embodiments, a controllable clickable monomer has the structure shown in any one of;

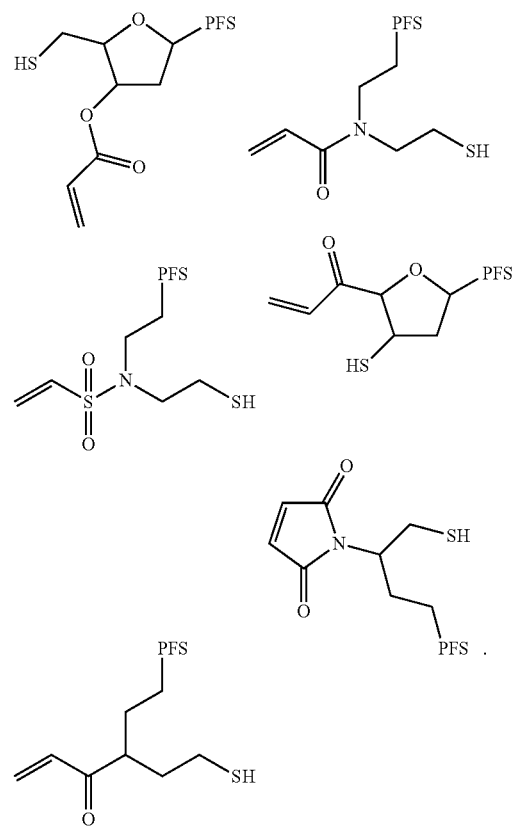

In some embodiments, a clickable sequence controllable monomer has an acrylamide backbone. In some embodiments, a clickable sequence controllable monomer has a α,β-unsaturated ketone backbone. In some embodiments, a clickable sequence controllable monomer has an optionally protected thiol-click acceptor such as a vinyl, vinyl ether, allyl ether, norbornene, vinyl sulfone, epoxy, acrylate, isocyanate, alkyne, methacrylate, maleimide, halide or alkyl extensions thereof.

In some examples, the sequence controllable monomer includes a vinyl ether moiety. In some examples, a vinyl moiety (including the vinyl moieties in an acrylate or vinyl ether) has the structure —CR$_5$═CR$_6$R$_7$, wherein R$_5$, R$_6$, and R$_7$ can independently be hydrogen, aryl, hydroxyl, carbonyl, carboxylic and other acids, amino, alkyl amide, thioether, cyclic, heterocyclic, hydrocarbyl, substituted hydrocarbyl, substituted heterocyclo, alkyl, substituted alkyl, acyl, —C(O)R, —C(O)OR, or —C(O)NR$_a$R$_b$, aryl or substituted aryl or heterocyclic ring.

In certain embodiments, the thiol moiety of the clickable sequence controllable monomer is protected. In certain embodiments, thiol-click acceptor of the clickable sequence controllable monomer is protected.

In some examples the sequence controllable monomer includes an A, G, T, U, or C nucleobase, although other nucleobases are contemplated, such as but not limited to those recited above in the listing of terms. In certain embodiments, the clickable sequence controllable monomer includes a nucleobase within the PSF group. In certain embodiments, the nucleobase of the clickable sequence controllable monomer is protected. In some embodiments, the click nucleic acid monomer further includes a linker, wherein the linker covalently links the nucleobase to the atom with the valency of 3 or more. In some examples, the linker includes —C(O)C—. In some embodiments, a PSF group has the structure:

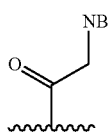

where NB is any nucleobase (for example A, T, G, C, or U), the amine on which may be protected.

In some embodiments, the optionally protected thiol has the structure:

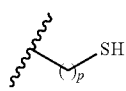

where p is an integer from 0 to 4, and wherein the methyl groups are optionally and independently substituted, for example substituted with aryl, hydroxyl, carbonyl, carboxylic and other acids, amino, alkyl amide, thioether, cyclic, heterocyclic, and alkyl extensions thereof. In a specific example, the optionally protected thiol has the structure:

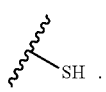

In some embodiments a thiol-click acceptor is an optionally substituted vinyl, vinyl ether, allyl ether, norbornene, isocyanate, vinyl sulfone, epoxy, acrylate, methacrylate, maleimide, halide and alkyl extensions thereof. In specific examples, a thiol-click acceptor has the structure set forth as one of:

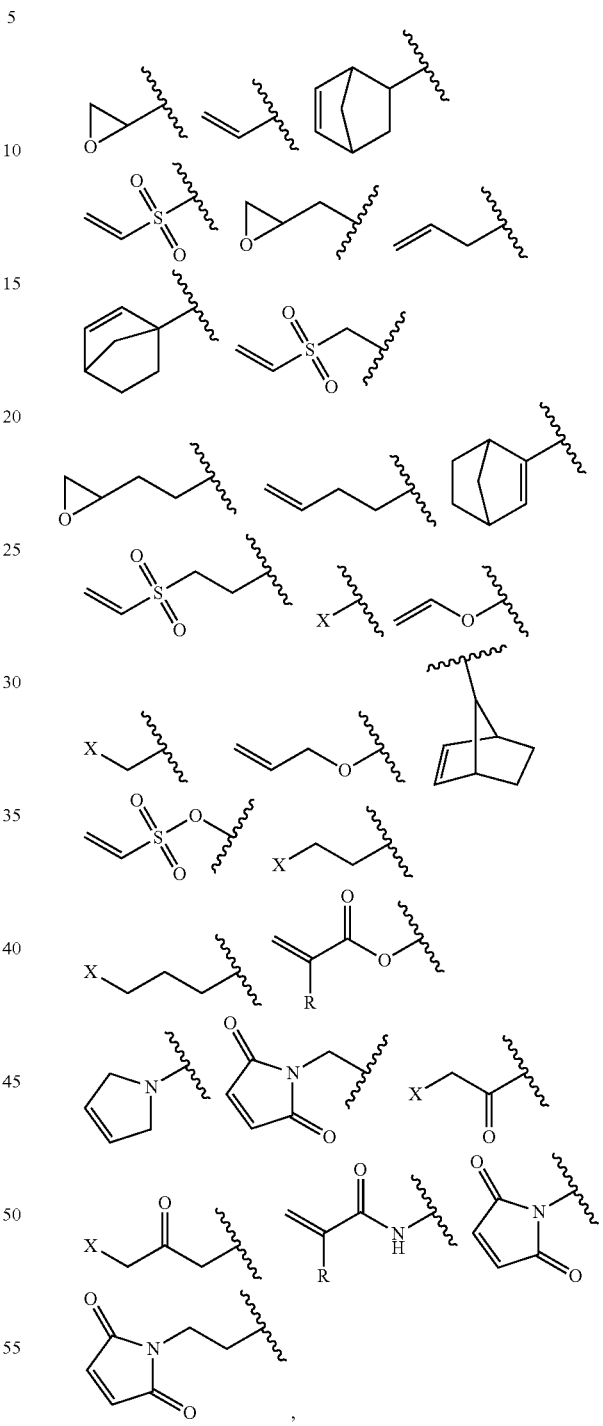

where X is a halide and R is a hydrogen or alkyl chain. In some examples, the thiol-click acceptor is an acceptor moiety as shown in the monomers shown in FIGS. 18A and 18B of International Application No. PCT/US2013/030538, filed Mar. 12, 2013, which are specifically incorporated herein in their entirety.

In some examples, the sequence controllable monomer includes an alkyne moiety. In some examples, the sequence controllable monomer includes a halide moiety. In some examples, the sequence controllable monomer includes an isocyanate moiety. In some examples, the sequence controllable monomer includes an epoxy moiety. In some examples, the sequence controllable monomer includes an acrylate moiety.

In some embodiments, a sequence controllable monomer includes an electron withdrawing group, for example situated next to the vinyl group. While not being bound by theory, it is believed that such groups in proximity to a vinyl group lead to enhanced reactivity of the vinyl group. Examples of electron withdrawing group(s) include hydroxy, alkoxy, mercapto, halogen, carbonyl, sulfonyl, nitrile, quaternary amine, nitro, or trihalomethyl. In some examples, where the electron withdrawing group is alkoxy, it generally corresponds to the formula —OR where R is hydrocarbyl, substituted hydrocarbyl, or heterocyclo. In some examples, where the electron withdrawing group is mercapto, it generally corresponds to the formula —SR where R is hydrogen, hydrocarbyl, substituted hydrocarbyl or heterocyclo. In some examples, where the electron withdrawing group is a halogen atom, the electron withdrawing group may be fluoro, chloro, bromo, or iodo; typically, it will be fluoro or chloro. In some examples, where the electron withdrawing group is a carbonyl, it may be an aldehyde (—C(O)H), ketone (—C(O)R), ester (—C(O)OR), acid (—C(O)OH), acid halide (—C(O)X), amide (—C(O)NR$_a$R$_b$), or anhydride (—C(O)OC(O)R) where R is hydrocarbyl, substituted hydrocarbyl or heterocyclo, R$_a$ and R$_b$ are independently hydrogen, hydrocarbyl, substituted hydrocarbyl or heterocyclo, and X is a halogen atom. In some examples, where the electron withdrawing group is a sulfonyl, it may be an acid (—SO$_3$H) or a derivative thereof (—SO$_2$R) where R is hydrocarbyl, substituted hydrocarbyl or heterocyclo. In some examples, where the electron withdrawing group is a quaternary amine, it generally corresponds to the formula —N$^+$R$_a$R$_b$R$_c$ where R$_a$, R$_b$ and R$_c$ are independently hydrogen, hydrocarbyl, substituted hydrocarbyl or heterocyclo. In some examples, where the withdrawing group is a trihalomethyl, it is preferably trifluoromethyl or trichloromethyl. In some examples, an optionally protected thiol-click acceptor is an optionally substituted vinyl, vinyl ether, allyl ether, norbornene, isocyanate, vinyl sulfone, epoxy, acrylate, methacrylate, maleimide, halide and alkyl extensions thereof.

It is contemplated that the disclosed monomers can be further modified, for example, to address any instability, toxicity, backbone stiffness, electronic charge, or solubility issues, for example, the basic monomer structure can be altered to facilitate, for example, the addition of anionic moieties to mimic better the DNA structure or by changing the number of backbone repeat unit atoms to optimize hybridization selectivity. In addition, the thiol and thiol-click acceptors moieties can be readily functionalized to add additional substituents, such as effector molecules, such as PEGs for improving solubility, peptides, contrast agents and dyes, and/or other oligonucleotides, such as DNA or RNA, As disclosed herein, reactive thiol-click acceptors, such as vinyl, vinyl ether, allyl ether, norbornene, vinyl sulfone, epoxy, acrylate, methacrylate, maleimide, halide and alkyl ene, alkyne, halide, isocyanate, epoxy, and thiol terminal groups are readily suited for further functionalization with various compounds such as PEGs for improving solubility, peptides, contrast agents and dyes, and/or other oligonucleotides, such as DNA or RNA. Further, the capability of further reaction is also the route to producing high molecular weight CNA sequences as purified, intermediate size 5, 10, or 20-mers of controlled sequence can be coupled in a single step to increase rapidly the number of bases in the sequence and achieve high molecular weights.

Figure 5:
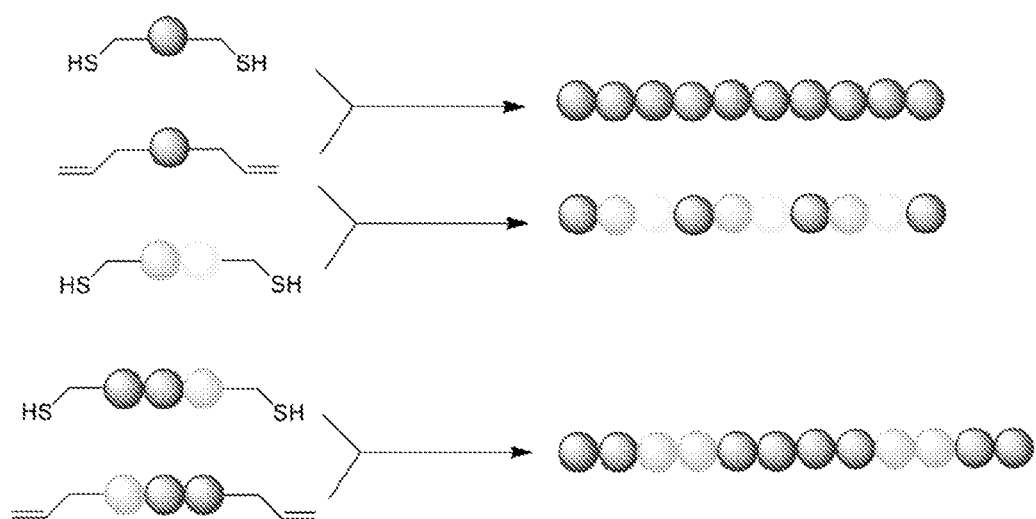
FIG. 5 is a schematic showing the sequence controlled synthesis of a polymer through "Click" by "Click" strategy

Disclosed are thiol-X polymers and methods of producing thiol-X polymers. A thiol-X polymer, includes at least one of the disclosed monomers. The thiol-X polymers can be of any length. The thiol-X polymers can be homogenous, or heterogenous, for example a thiol-X polymer can be composed of a single type of disclosed monomer or any combination of monomers disclosed herein. In some embodiments, the disclosed thiol-X polymers include the monomers disclosed herein and/or the CNA monomers disclosed in the International Application No. PCT/US2013/030538, filed Mar. 12, 2013, which is specifically incorporated herein in its entirety. Homopolymerization has the capacity for forming high molecular weight linear polymers either by thiol-Michael or thiol-ene reactions. Dimer repeating polymers can be made by polymerizing dithiol mono-mers A with diene monomer B to form an AB repeating structure, more complicated homopolymers with different repeating units can also be achieved by starting with more complicated monomers as shown in FIG. 5. Click-by-click sequential synthesis uses the thiol-Michael addition reaction to couple monomers, sequentially followed by thiol-deprotection. The efficiency of the thiol-Michael reaction assures that such reactions go to completion and that solid phase synthesis is not necessary. Sequential monomer addition, polymerization and deprotection steps result in quantitative addition of each repeat unit to the polymer. Terminal, thiol-ene reactive vinyls can then be used to couple two partially completed strands to form a longer sequence or can be used to couple the desired sequence to other chemical moieties such as fluorophores, peptides or other DNA strands, as well as to surfaces, particles or other substrates. In certain embodiments, a thiol-X polymer has one thiol, one vinyl group, or dithiol and divinyl groups. In some embodiments, a thiol-X polymer includes natural nucleobases, modified nucleobases or a combination thereof. In some embodiments, a thiol-X polymer includes one of more amino acids or amino acid sidechains. In certain embodiments, a thiol-X polymer includes a chemical moiety to alter conformation by external stimuli, such as light. In certain embodiments, a thiol-X polymer is covalently linked to an effector molecule, such as a detectable marker and/or a bioactive compound.

Effector molecules, such as therapeutic, diagnostic, or detection moieties or others molecules can be linked a disclosed polymer molecule, using any number of means known to those of skill in the art. Both covalent and noncovalent attachment means may be used. The procedure for attaching an effector molecule to a thiol-X polymer molecule according to the chemical structure of the effector and which end of the CNA molecule attachment is to occur. For example Polypeptides typically contain a variety of functional groups; e.g., carboxylic acid (COOH), free amine (—NH$_2$) or sulfhydryl (—SH) groups, which are available for reaction with a suitable functional group (for example the thiol or TCA moiety present on either end of the thiol-X polymer molecule) on the thiol-X polymer result in the binding of the effector molecule. This attachment can be direct or through a linker and may involve attachment of any of a number of linker molecules such as those available from Pierce Chemical Company, Rockford, Ill. The linker can be any molecule used to join the thiol-X polymer to the effector molecule. The linker is capable of forming covalent bonds to both thiol-X polymer and to the effector molecule. Suitable linkers are well known to those of skill in the art and include, but are not limited to, straight or branched-chain carbon linkers, heterocyclic carbon linkers, or peptide linkers.

In some circumstances, it is desirable to free the effector molecule from the thiol-X polymer. Therefore, in these circumstances, such conjugates will comprise linkages that are cleavable.

In view of the large number of methods that have been reported for attaching a variety of radiodiagnostic compounds, radiotherapeutic compounds, label (e.g. enzymes or fluorescent molecules) drugs, toxins, and other agents, one skilled in the art will be able to determine a suitable method for attaching a given agent to an Thiol-X polymer.

Disclosed herein are methods of producing a CNA monomer, for examples as shown below:

Approach 1. Thio-Michael Monomers' Library Generation

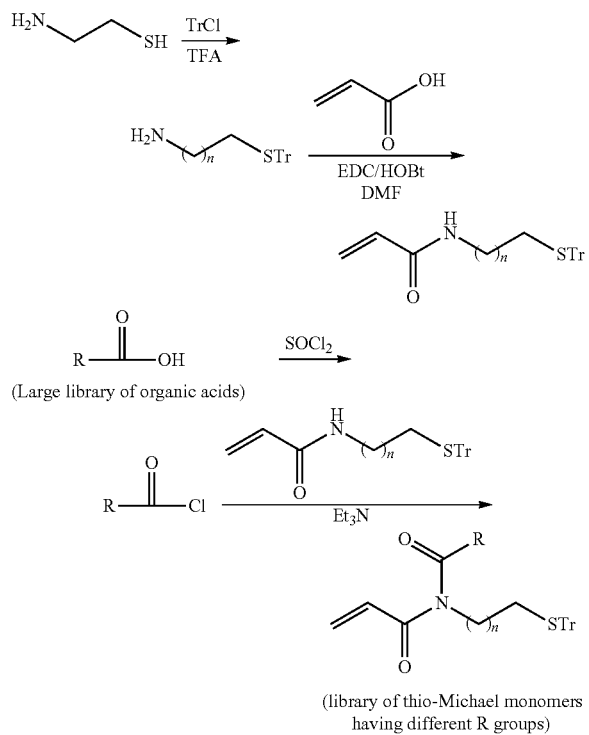

R = amino acid, sugar, other liphphilic/polar/ampniphilic groups
m, n = 1, 2, 3 . . .

Approach 2. Thio-Ene Monomers' Library Generation

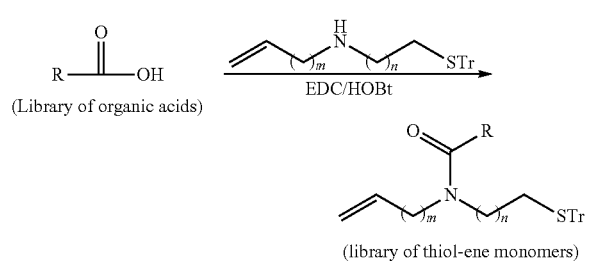

In both examples, the monomer is synthesized from several simple molecular constituents, allowing precise, atomic level monomer design. Having this synthetic control over the monomer structure further enables simple structural variations as a possible contingency of poor solubility or hybridization efficiency or as further optimization of hybridization stability.

Disclosed are thiol-X polymers and methods of producing a thiol-X polymer. A thiol-X polymer, includes at least two of the disclosed CNA monomer. The thiol-X polymers can be of any length. The thiol-X polymers can be homogenous, or heterogeneous, for example a thiol-X polymer can be composed of a single type of disclosed monomer or any combination of monomers disclosed herein or in International Application No. PCT/US2013/030538, filed Mar. 12, 2013, which is specifically incorporated herein in its entirety.

Disclosed herein are methods of producing thiol-X polymers. To create thiol-X polymers, the monomers are polymerized through a variety of methods including solid-phase, in solution, in microarray-style formats, and in bulk polymerization to generate homopolymers. An example of polymerization is shown:

Thiol-Click Polymerization to Obtain Mixed-Sequence Polymers

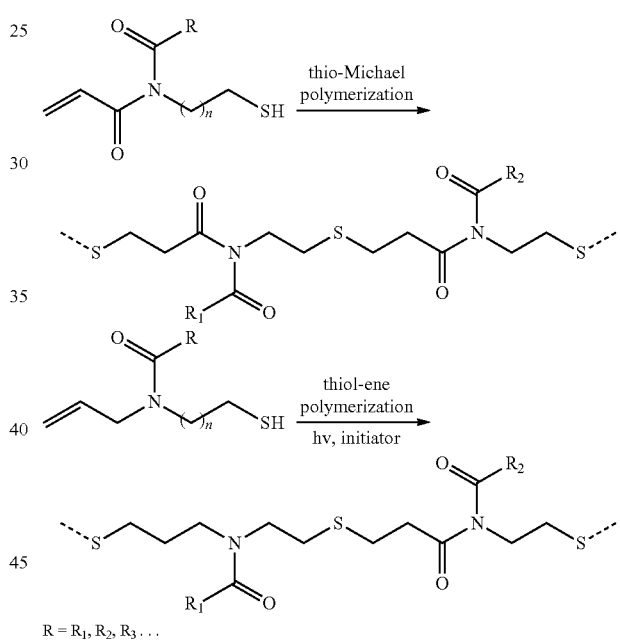

R = R$_1$, R$_2$, R$_3$ . . .

Additional methods of thiol-X polymer production are shown in International Application No. PCT/US2013/030538, filed Mar. 12, 2013, which is specifically incorporated herein in its entirety. In some examples the polymerization reaction is photoinitiated. The reactions can be photoinitiated with a photoinducible photoactivator, for example with hydroxy-cyclohexyl-phenyl-ketone. In some examples, the reaction is photoinitiated with between about 0.001 wt % and about 1.0% hydroxy-cyclohexyl-phenyl-ketone, such as about 0.01 wt % hydroxy-cyclohexyl-phenyl-ketone, 0.01 wt % hydroxy-cyclohexyl-phenyl-ketone or 1.0 wt % hydroxy-cyclohexyl-phenyl-ketone. In some examples, the photoactivator is activated at about 1 to about 100 mW/cm$^2$ light having a wavelength between about 350 and 410 nm. In a specific example, the photoactivator is activated with light of about 10 mW/cm$^2$ with a wavelength of about 365 nm.

The ability to photoinitiate the reaction is of great innovation. With this capability, arrays of sequences (akin to the Affymetrix DNA chips) are readily produced on a single chip in a facile manner for biodetection, origami, or other applications.

C. Exemplary Methods of Use i. Exemplary CNA Applications.

CNA applications include biodetection, development of a SELEX-like process, and replication of complementary DNA or CNA sequences. Targeting similar amplification and outcomes as PCR, an exponential amplification process through which CNA strands are replicated from complementary DNA or CNA strands by in situ hybridization and selective ligation of oligomeric CNAs. This process will function as one means of producing large volumes of high molecular weight sequences and be appropriate for implementation in biodetection, where substrate amplification is critical to detection.

a. Probes and Primers

The disclosed thiol-X polymers can be used as probes and/or primers capable of binding to and detecting a target nucleic acid. Typically, such probes and primers are between 6 and 40 nucleotides in length, such as 6, 7, 8, 9, 10, 11, 12, 13, 14, 15, 16, 17, 18, 19, 20, 21, 22, 23, 24, 25, 26, 27, 28 29, 30, 31, 32, 32, 34, 35, 36, 37, 38, 39, or 40 nucleotides in length and are capable of hybridizing a target nucleic acid, although longer and/or shorter sequences are contemplated, for example for southern blots and other applications. Thus in some examples, a probe or primer is greater that 40 nucleotides in length, such as at least 50 nucleotides, at least 60 nucleotides, at least 70 nucleotides, at least 80 nucleotides, at least 90 nucleotides, at least 100 nucleotides, at least 150 nucleotides, at least 200 nucleotides, at least 250 nucleotides, at least 500 nucleotides, or even at least 1000 nucleotides in length.

In some embodiments, a thiol-X polymer probe and/or primer is detectably labeled, either with an isotopic or non-isotopic label, alternatively the target nucleic acid (such as an influenza nucleic acid) is labeled. Non-isotopic labels can, for instance, comprise a fluorescent or luminescent molecule, biotin, an enzyme or enzyme substrate or a chemical. Such labels are preferentially chosen such that the hybridization of the probe with target nucleic acid can be detected. In some examples, the probe is labeled with a fluorophore. In some examples, a thiol-X polymer, such as a probe, is linked to a solid substrate, such as a bead and/or an array. In some embodiments, a disclosed thiol-X polymer is a molecular beacon probe (see FIG. 8). Because of the high-fidelity binding capability of thiol-X polymers, these can be employed as stem loop oligonucleotides or molecular beacons for biomolecular recognition reactions. Molecular beacons can be used to monitor real-time PCR amplification, detection of mutation and pathogens etc. For the simplest of the objective, the thiol-X polymer molecular beacon is designed containing a sequence complementary to the target and having a fluorophorequencher pair at the 5'- and 3'-termini. In absence of the target, the close proximity of the fluorophore-quencher pair represses fluorescence. When the target is present, the thiol-X polymer complexes with the target and the fluorescence can be detected, b. Quadruplex Forming and Disrupting CNA Oligos Guanine-rich oligo sequences form secondary structures known as G-quadruplex, which are stabilized by cationic coordination and hydrogen bonding. G-quadruplexes are often found in telomeres and promoter regions. As G-rich telomeres are constantly recruited by telomerases in cancer cells, targeting G-quadruplex sequences offers a way to induce apoptosis. Using the disclosed CNA chemistry, thiol-X polymers are prepared having consecutive cytidine sequences (complementary to G-rich sequences) that bind strongly with G-rich sequences and disrupt the quadruplex. These type of lipophilic G-quadruplexes may bind applications in nanoscale assemblies.

c. Detection and Identification of a Target Nucleic Acid

A major application of the thiol-X polymer primers and probes disclosed herein is for the detection of a target nucleic acid in a sample, such as a biological sample. The methods described herein may be used for any purpose where the detection of a target nucleic acid is desirable, including diagnostic and prognostic applications, such as in laboratory and clinical settings. Appropriate samples include any conventional environmental or biological samples, including clinical samples obtained from a human or veterinary subject, including, but not limited to, cells, tissues (for example, lung, liver and kidney), bone marrow aspirates, bodily fluids (for example, blood, serum, urine, cerebrospinal fluid, bronchioalveolar levage, tracheal aspirates, sputum, nasopharyngeal aspirates, oropharyngeal aspirates, saliva), eye swabs, cervical swabs, vaginal swabs, rectal swabs, stool, and stool suspensions.

d. CNA Arrays

Also disclosed are arrays containing a plurality of homogeneous or heterogeneous thiol-X polymer probes for the detection of target nucleic acids. Arrays are arrangements of addressable locations on a substrate, with each address containing a thiol-X polymer, such as a probe. In some embodiments, each address corresponds to a single type or class of thiol-X polymer, such as a single probe, though a particular thiol-X polymer may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

Any sample potentially containing, or even suspected of containing, a target nucleic acid, including nucleic acid extracts, such as amplified or non-amplified DNA or RNA preparations may be targeted and analyzed. A hybridization signal from an individual address on the array indicates that the probe hybridizes to a nucleotide within the sample. This system permits the simultaneous analysis of a sample by plural probes and yields information identifying the influenza nucleic acids contained within the sample.

The nucleic acids may be added to an array substrate in dry or liquid form. Other compounds or substances may be added to the array as well, such as buffers, stabilizers, reagents for detecting hybridization signal, emulsifying agents, or preservatives.

Within an array, each arrayed thiol-X polymer is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

e. Nucleic Acid "Origami" and Directed Assembly

The disclosed thiol-X polymers can be used in nucleic acid origami and directed assembly applications, for example as a nucleic acid staple. Nucleic acid origami is the nanoscale folding of nucleic acids to create arbitrary two and three-dimensional shapes at the nanoscale. The specificity of the interactions between complementary base pairs make DNA a useful construction material, through design of its base sequences. Nucleic acid origami involves the folding of a long single strand of viral DNA aided by multiple smaller "staple" strands. In some examples, images are drawn with a raster full of a single long DNA molecule. This design is then fed into a computer program that calculates the placement of individual staple strands. Each staple binds to a specific region of the DNA template, and thus due to Watson-Crick base pairing, the necessary sequences of all staple strands are known and displayed. The DNA is mixed, then heated and cooled. As the DNA cools, the various staples pull the long strand into the desired shape. Designs are directly observable via several methods, including atomic force microscopy, or fluorescence microscopy when DNA is coupled to fluorescent materials Such self-assembly of nucleic acid can be used for synthesis of nanostructures under relatively mild conditions, for applications such as enzyme immobilization, drug carry capsules, and nanotechnological self-assembly and directed patterning of materials on surfaces and in the bulk solution or suspension, for example nanoparticles with desired characteristics.

f. Aptamers and Catalytic Molecules

In some embodiments, the thiol-X polymers disclosed herein are used to make an aptamer that specifically binds a particular target molecules. An initial thiol-X polymer library of materials incorporates naturally occurring nucleobases, for example distinct thiol-X polymers that are 20 repeat units in length thiol-X polymers of 30 repeat units in length, and broadly resemble classical aptamer structures though with the enhanced physicochemical capabilities associated with folding, stability, and scalability afforded by the click approach. In some examples, additional libraries of compounds are developed based on incorporation of non-native bases into the thiol-X polymer library to enhance chemical variability and the development of a second, completely independent library that mimics peptidic structures. This latter approach to develop thiol-enzymes (TEZs) would create and assemble a family of at least 10 distinct monomer structures and much larger range of physicochemical structures that would result from the assembly of all random sequences of these materials. The clickable nucleic acids and related families of materials will enable the rapid synthesis, screening, sequencing, and scale-up of folded, non-natural, sequence defined thiol-X polymers that interact specifically, strongly, and selectively with the targeted compounds.

Screening of non-natural thiol-X polymer libraries to identify binders and catalysts is done with a SELEX-like approach in which we demonstrate with the thiol-X polymer library the ability to bind oligonucleotides with specificity and strength. This approach includes (i) the library synthesis, (ii) initial selection of the affine molecules, (iii) amplification of those molecules, and (iv) cyclic improvements in the binding capacity of the selected molecules. An affinity compound from one library that binds to a selected small molecule target (i.e., a pharmaceutical agent) and to an oligonucleotide. In certain examples a screen for catalytic activity of the molecules is developed as well and demonstrating the capacity based on that screen to amplify and optimize the structure of library molecules with catalytic activity, specifically for alkyl ester hydrolysis.

Figure 6:
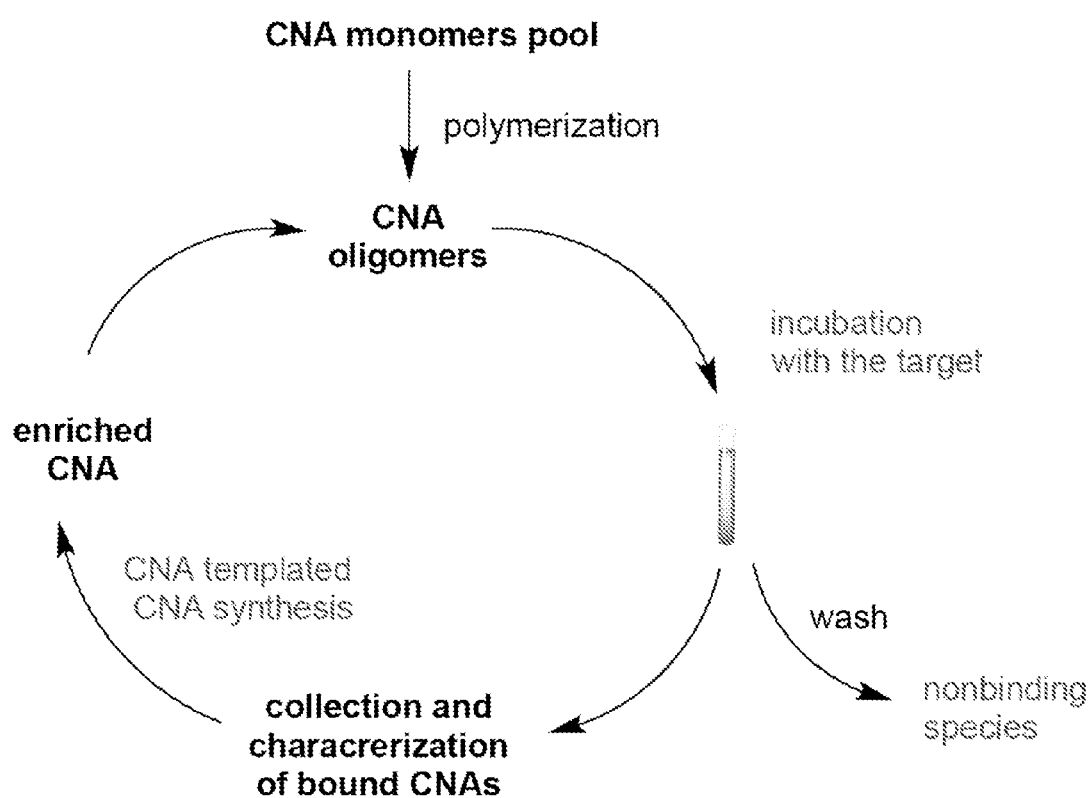
FIG. 6 is a schematic showing the selection of target-specific CNAs through a modified SELEX process.

Aptamer technology is currently considered as a potential alternative to antibodies. Aptamers are short oligonucleotide (or peptide) sequences having specific affinity to the target molecule of interest. The disclosed thiol-X polymers can be employed as aptamer mimic to selectively bind the target molecule of choice, which include but not limited to metal ions, small organic compounds like dyes, sugars, antibiotics etc or large organic molecules like proteins or complex targets like living cells and pathogens. The aptamer technology is based on the recognition of the molecular target by stable and sequence dependent 3D conformation of the aptamer. The simple chemical structure also makes it amenable for further chemical modifications. Aptamers are generally selected using SELEX (systematic evolution of ligands by exponential enrichment) approach, which consists of steps like oligonucleotide library creation, incubation with target molecule, selection and isolation of bound aptamers, and amplification (see FIG. 6). Using thiol-X click chemistries, a large library of thiol-X polymers is created having broad sequence and molecular weight range. The library can be easily created using the disclosed thiol-X polymer technology by changing the stoichiometry and thiol-X polymerization conditions. The unbound thiol-X polymers are then washed out and selected thiol-X polymers are collected and purified. The selected thiol-X polymers are analyzed for sequence determination and further used for enzymatic or non-enzymatic amplification process. Practical applications of the selected thiol-X polymers include but not limited to development of new drugs, therapeutic tool, bio-imaging, hazard detection, disease diagnosis and drug delivery etc. The advantage of disclosed thiol-X polymer technology is that a large library can be created very easily from using the thiol-X polymerization chemistry, the thiol-X polymers bind more strongly than their natural counterparts and can be prepared in much lower cost. The chemistry also allows for the inclusion of all types of modified nucleobases, and entities not related to nucleobases including amino acids, sugars, and other polar and lipophilic molecules. The conformation of the CNAs also can be tuned by incorporating chemical entities (azobenzene etc) that responds to external stimuli (light etc) and can take different in space arrangements.

Figure 7:
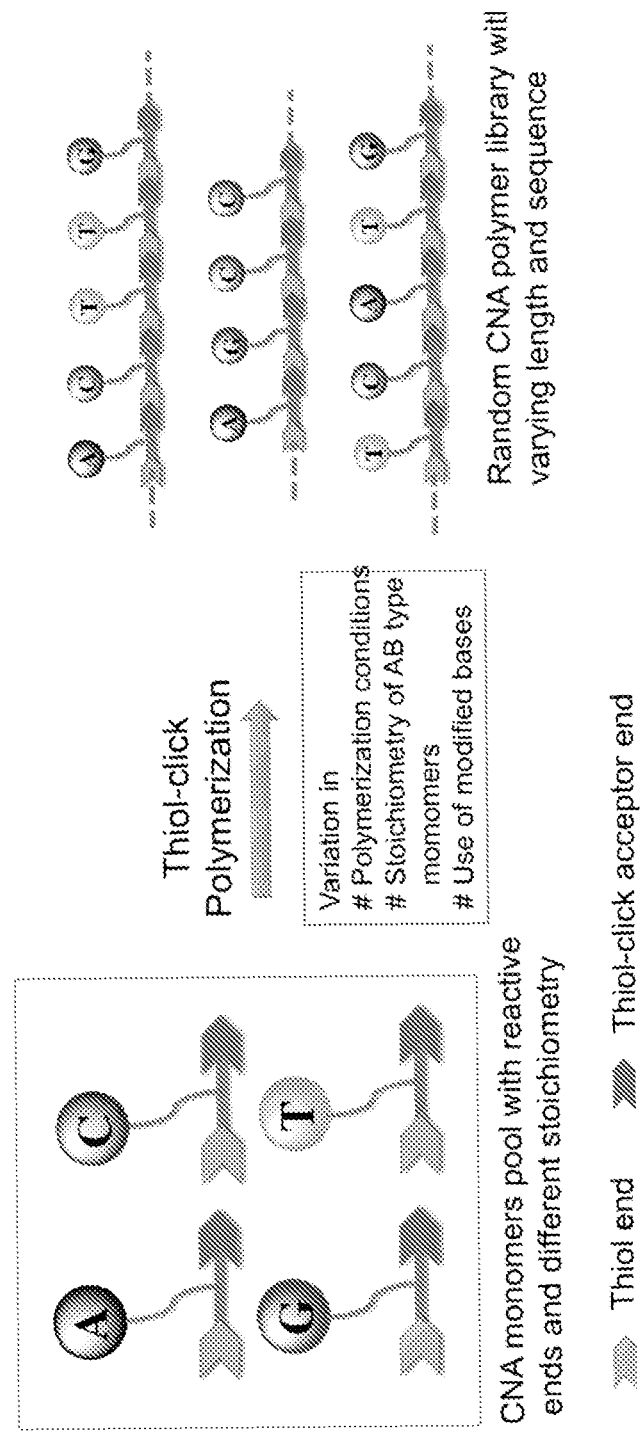
FIG. 7 is a schematic showing thiol-click polymerization.

The synthetic strategy for thiol-X polymers can be extended to incorporate other chemical entities that can be virtually any acids including but not limited to amino acids, modified nucleobase acetic acids, lipophilic and polar acids, sugars, cationic and anionic groups etc. In this embodiment, monomer backbones having general structure of TCA-ZH-T is exemplified, where Z is the atom to connect the new chemical entity (e.g. the acid in this case), T is the optionally protected thiol and TCA is the optionally protected thiol-click acceptor. The synthetic routes have been demonstrated for obtaining a library of such kind of monomers from a pool of different acids, together with a common backbone having T and TCA moieties. The general synthetic route, taking thio-acrylate monomer as an example is shown in (see FIG. 7), however, this can be extended to other thiol-click reactions.

g. mRNA Isolation with polyT-Functionalized Solid Support

Most eukaryotic mRNAs contain tracts of terminal polyA chain that is employed to isolate mRNA from total cell-extract using affinity chromatography with solid supports (magnetic beads, celluloses etc), functionalized with polyT chains (known as mRNA isolation kits). However, these kits are expensive because of high cost of preparing the DNA and the conjugate. Using present CNA oligomers, said solid supports with suitable terminal groups (including but not limited to thiols, acrylates) can be prepared in a single step. As an example, thiol-functionalized magnetic beads are copolymerized with thiol-ene type of monomer to get the poly-T ornamented mRNA-affinity reagent. These can be used to isolate mRNA from a total cell extract.

ii. In Vivo CNA Applications.

In light of their unique chemical and physical properties, thiol-X polymers have considerable potential for in vivo applications. Of interest is the potential for thiol-X polymers to transverse the outer cell membrane. Given thiol-X polymers hydrophobicity and neutral backbone, thiol-X polymers will penetrate the lipid membrane of cells and have intrinsically high cell permeability. Importantly, the ability of thiol-X polymers to enter cells can be optimized by chemically tailoring the liphophilicity of the thiol-X polymer monomers. This ability, combined with the in vivo stability and high affinity and specificity of thiol-X polymers towards complementary RNA and DNA is exploited for RNA and/or DNA interference. Specifically, thiol-X polymers will be used to silence target genes and entire pathways. This use has broad implications for therapeutics and for mechanistic studies involving gene regulation. Moreover, this cell-penetrating ability is useful for delivery of exogenous dyes or therapeutic molecules, including proteins.

a. Therapeutic Compositions

The disclosed thiol-X polymers can be administered in vivo to a cell or subject. Generally, it is desirable to prepare the compositions as pharmaceutical compositions appropriate for the intended application. Accordingly, methods for making a medicament or pharmaceutical composition containing the thiol-X polymers as described herein above are included. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake by target cells, such as tumor cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of the thiol-X polymer dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the thiol-X polymer in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Administration of therapeutic compositions can be by any common route as long as the target tissue is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. Such pharmaceutical compositions are usually administered as pharmaceutically acceptable compositions that include physiologically acceptable carriers, buffers or other excipients.

The pharmaceutical compositions can also be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well known parameters.

Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders.

When the route is topical, the form may be a cream, ointment, salve or spray. An effective amount of the pharmaceutical composition is determined based on the intended goal, for example vaccination of a human or non-human subject. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes a thiol-X polymer.

When administering an nucleic acid, facilitators of nucleic acid uptake and/or expression can also be included, such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, for example, *Liposomes: A Practical Approach*, RPC New Ed., IRL Press, 1990). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename LIPOFECTIN®, and DOTAP (1,2-bis(oleyloxy)-3-(trimethylammonio)propane). See, for example, Felgner et al., *Proc. Natl. Acad. Sci. U.S.A.* 84:7413-7416, 1987; Malone et al., *Proc. Natl. Acad. Sci. U.S.A.* 86:6077-6081, 1989; U.S. Pat. Nos. 5,283,185 and 5,527,928, and International Publication Nos. WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, for example, International Publication No. WO 93/18759) and membrane-permeabilizing compounds such as GALA, Gramicidine S and cationic bile salts (see, for example, International Publication No. WO 93/19768).

An appropriate effective amount can be readily determined by one of skill in the art. Such an amount will fall in a relatively broad range that can be determined through routine trials, for example within a range of about 10 µg to about 1 mg. However, doses above and below this range may also be found effective.

Therapeutic compositions that include a disclosed therapeutic agent can be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(-)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

A disclosed CNA can also be conjugated with a detectable marker. For example, a detectable marker capable of detection by a diagnostic imaging techniques (such as CT scans, MRIs, ultrasound, fiberoptic examination, and laparoscopic examination). Specific, non-limiting examples of detectable markers include radioactive isotopes and heavy metals or compounds (for example super paramagnetic iron oxide nanocrystals for detection by MRI). Means of detecting such detectable markers are well known to those of skill in the art. Thus, for example, radiolabels may be detected using photographic film or scintillation counters.

The pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results, for example to alleviate one or more symptoms or detectable conditions associated with a targeted disease or condition as set forth herein or in an amount sufficient to image a tumor.

The appropriate dose will vary depending on the characteristics of the subject, for example, whether the subject is a human or non-human, the age, weight, and other health considerations pertaining to the condition or status of the subject, the mode, route of administration, and number of doses, time and route of administration, other drugs or treatments being administered concurrently, as well as the specific pharmacology of the therapeutic compositions for eliciting the desired activity or biological response in the subject. Dosage regimens can be adjusted to provide an optimum prophylactic or therapeutic response.

A therapeutically effective amount is also one in which any toxic or detrimental side effects of the compound and/or other biologically active agent is outweighed in clinical terms by therapeutically beneficial effects. A non-limiting range for a therapeutically effective amount within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight per dose to about 10 mg/kg body weight per dose.

b. Inhibition of Neurodegenerative Diseases

Genomic analyses have shown that abnormal expansions of simple repeating sequences in the genome are responsible for a wide class of genetic disorders. At least 16 human-inherited neurological diseases are caused by simple trinucleotide repeat expansions (CAG, CUG etc.) that are collectively known as trinucleotide repeat disorder. This class of diseases includes Huntington disease (caused by CAG repeat), myotonic dystrophy type 1 (caused by CUG repeat), Fragile X syndrome (caused by CGG repeat) and several types of ataxia. Additionally, expanded hexanucleotide (GGGGCC) repeat in C9ORF72 gene has been identified as the cause for amyotrophic lateral sclerosis (ALS), Alzheimer's disease and frontotemporal dementia. The telomere is also consists of repeat sequences of TTAGGG, which is a lucrative cancer target. ASO-based approaches targeting these sequences showed promising results to treat the corresponding diseases.

Unfortunately, whether native DNA, PNAs or any other type of specific oligonucleotide sequence, each of these methodologies requires a step-by-step synthesis to form a desired sequence. Currently, there is no scalability afforded by any methodology for producing oligonucleotides—producing a sequence of 20 bases requires approximately twice as many steps as producing a sequence of 10 bases—even if there is inherently a repeating structure as is the case for the trimer in HD.

Trinucleotide repeat disorders are a class of human-inherited neurological diseases that are caused by simple trinucleotide repeat expansions or in other words DNA sequences in which a specific collection of three nucleobases repeats itself over and over. Together, these neurodegenerative diseases affect hundreds of thousands of individuals worldwide. Huntington Disease (HD) has the highest occurrence among all trinucleotide repeat disorders with an incidence of 1 per 10,000 individuals. The symptoms of HD include cognitive impairment, violent choreiform movement, as well as severe mood and behavioral disorders that are chronic and progressive. HD occurs due to an increased number of CAG repeat units in affected individuals (i.e., ~45 trimer repeats in HD cases as compared to ~20 for unaffected individuals). Ultimately, this increased number of trimer repeat units codes for the generation of a polyglutamine tract which is neurotoxic and broadly responsible for the symptoms of HD. Currently, there is no curative treatment available for HD patents. However, recent advances in oligonucleotide-based approaches using RNAi and antisense oligonucleotide (ASO) technology have opened up avenues to treat previously untreatable genetic diseases. Specifically, based on the hypothesis that the expanded mutant CAG repeat in HD forms a structure that is susceptible to silencing, the Corey group recently successfully employed a poly(CTG) sequence (~18-20 nucleotides) of a DNA mimic (i.e., peptide nucleic acids (PNAs)) to selectively inhibit polyglutamine production.

A novel class of biofunctional oligonucleotides, Clickable Nucleic Acid or CNAs is created that utilize the thiol-Michael and thiol-ene 'click' reactions to form the desired repeating base sequence in a single step from an appropriately functionalized monomer. This one step polymerization approach, shown in FIG. 10, along with conventional step-by-step synthesis, has several distinct advantages that enhance its significance, particularly, (i) use of click chemistry to enable desirable reaction features and couplings, (ii) initiation of the reaction by nucleophiles or bases, (iii) facile scalability and purification, and iv) the formation of a polymer with a thio-ether backbone to enhance stability. CNAs can be modified further with molecules such as PEG, cell penetrating peptides, or other targeting compounds to address solubility or cellular uptake issues.

The approach to target HTT will commence from the preparation of the complementary CNA having sequence poly(GTC) and its ability to inhibit HTT expression will be studied in HD patient derived cell lines. Specifically, the methodology is i) synthesize guanine, thymine and cytosine base-functionalized thiol-ene or thiol-Michael monomers of appropriate molecular structure and reactive functionality with suitable protecting group chemistries. ii) react those monomers in stepwise fashion to prepare the suitably functionalized GTC subunit with polymerizable ends. iii) demonstrate single step thiol-X polymerization of GTC subunit to obtain the poly(GTC) oligonucleotide. iii) carry out biophysical characterization of poly(GTC) oligomers for binding capability with target DNA through melting temperature and CD experiments. iii) examine the cytocompatibility and cellular uptake properties of the oligomers. iv) demonstrate its ability to inhibit HTT gene in Huntington disease cell lines (GM04281 etc.) using western blot assays and analyze of their allele specificity.

In some examples the backbones of the monomer units will be further functionalized with hydroxyl, amine or arginine groups to address solubility or toxicity issues which might have aroused. Further, the oligos will be coupled with cell penetrating peptides, poly-amines, PEG side chains to aid the cellular uptake. For antisense properties demonstration, along with the western blot experiments we plan to create transiently transfected GFP-reporter cell lines with HTT expression and cell based GFP assays will be performed to quantify the effect of poly(GTC) CNA oligomers.

Figure 10:
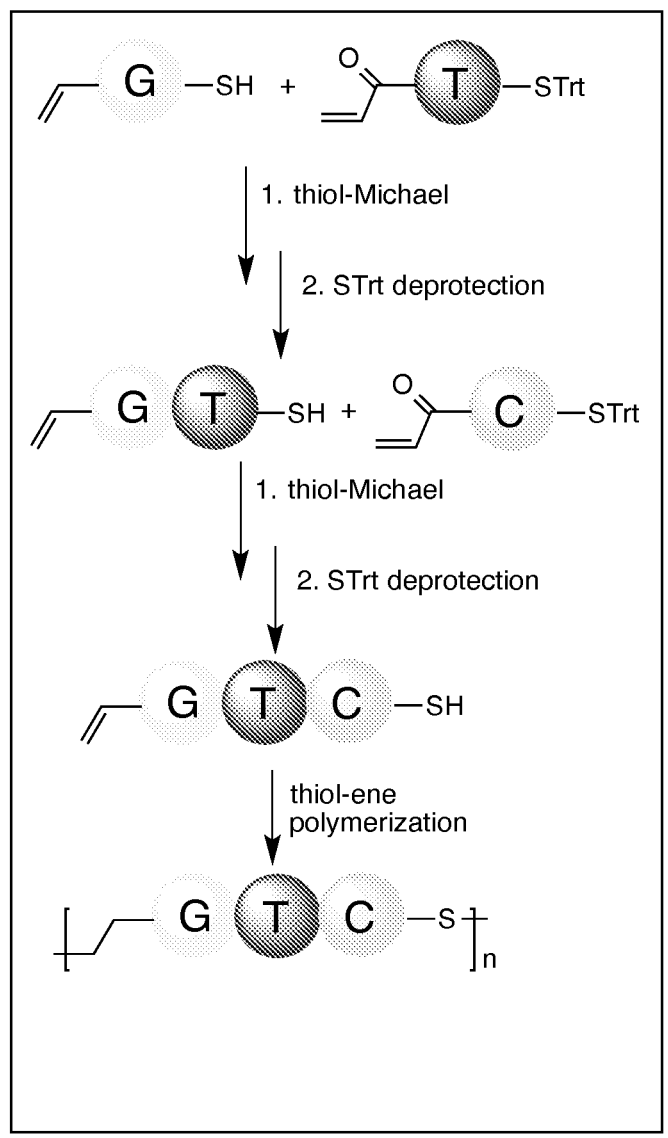
FIG. 10 is a schematic showing a synthetic strategy to prepare a reactive-end CTG trimer and its polymerization to get a poly(CTG) oligo.

The synthetic target sequence of CNA oligomers is the present case is poly(GTA). In this strategy, GTA trimer will be first synthesized as a monomer for thiol-ene polymerization. For GTA trimer synthesis, G thiol-ene type monomer will be used for coupling to T thiol-Michael type monomer and A thiol-Michael type monomer sequentially. After that, deprotection of Trt group will release free thiol for thiol-ene polymerization. The thiol-ene polymerization of GTA trimer will yield poly(GTA)n as CNA oligomer which is enable to bind to poly(CAG)n in DNA as shown in FIG. 10. Other efficient reactions can be used, such as the thiol-Michael reaction of CUAAC reactions for the final polymerization and suitable trinucleotide monomers with reactive ends.

D. Kits

The disclosure also provides kits that include one or more CNA molecules of this disclosure in one or more containers. In some examples, CNA molecules are lyophilized, and reconstituted before administration to a subject or any other use. Kits can optionally include other agents, such as pharmaceutically acceptable carriers, instructions, and the like.

Aspects of the forgoing are illustrated by the following non-limiting examples.

EXAMPLES

Example 1

Production of CNA Polymers

Using just four monomers, 420 (~1012) unique polymers of 20 repeat units and 430 (~1018) unique polymer sequences of 30 repeat units are formed. Additional libraries developed will expand further on these capabilities.

The selection of monomers and libraries is performed based on a combination of theoretical and experimental validation. The vast range of possible nucleobases, backbone structures, and other modifications renders it impossible to synthesize and experimentally assess all of the possible monomer molecules. Theoretical assessment of the variety of monomeric/polymeric species in the libraries is used to narrow the synthetic scope and focus on the monomers that provide the greatest opportunity for specific, strong binding. In particular, the computational and experimental efforts are strongly coupled through frequent and detailed feedback of simulations and experimental results. The computational effort incorporate classical molecular simulations that utilize quantum mechanically derived force fields which are validated by comparing trends in thermal stability of a small validation set of CNA complexes with both the small molecule and DNA targets as a function of length, base, sequence and backbone chemistry. Upon validation, quantum and molecular simulations expand to a larger parameter set of backbone chemistries, strand sequences (composition and sequence of bases along the strand) and strand length to guide the synthesis of an expanded library of CNA-based oligonucleotides and eventually TEZs.

Figure 3:
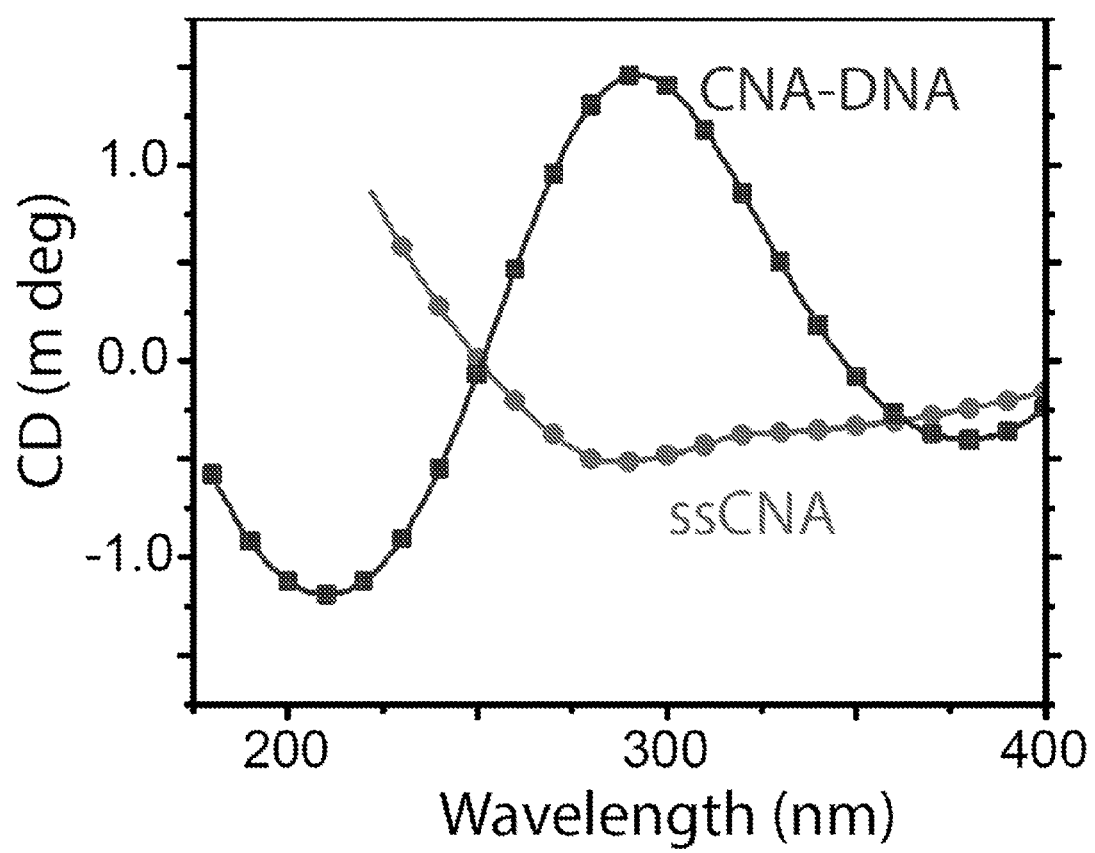
FIG. 3 is a CD spectrograph of a C-CNA oligomer (10 bases) with and without complementary G-DNA at 25° C. (top) and melting temperatures determined via a temperature sweep (bottom). The melting temperature ($T_m$) is larger for CNA-DNA hybrids than for DNA-DNA hybrids and is more affected by single base mismatches, indicating a higher degree of stability and selectivity, respectively.

Results obtained demonstrate that this methodology is highly successful. A CNA oligomer was fabricated via a thiol-ene polymerization. The product was purified by ethanol precipitation and confirmed using MALDI-TOF mass spectroscopy. CD spectroscopy of oligomeric C-CNA and G-DNA exhibits optical activity characteristic of secondary structure (FIG. 3). Moreover, a temperature sweep to 90° C. (at 2° C./min) reveals a disassociation or 'melting' temperature that is 20° C. in excess of DNA-DNA binding equivalents (FIG. 3); that is, the complementary CNA-DNA binding is significantly more stable than the analogous DNA-DNA hybrid. When repeating the hybridization experiment except with a DNA strand that contained a single change in the sequence (i.e., a single nucleotide polymorphism or SNP), the effect of a single base mismatch was a dramatic destabilization of the CNA-DNA association (>20° C. decrease in Tm as compared to a 9° C. decrease in Tm for the analogous DNA/DNA pair), indicating that CAN materials are exceptionally sensitive to DNA mismatches (i.e., SNPs) and ultimately the overall DNA sequence as needed here.

Example 2

SELEX

A method called systematic evolution of ligands by exponential enrichment (SELEX) has been used to generate high-affinity nucleic acid ligands or aptamers. The basic SELEX process starts from a library of synthetic DNA oligonucleotides with random sequences. Building on this approach to enhance the capabilities of this process by implementing CNA libraries and by developing purely chemical approaches to substrate amplification.

Specifically, once the CNA polymer libraries are formed by a simple random polymerization of the desired monomers, the next element in developing selective ligands will use a SELEX-like, cyclic process of alternating affinity selection, error-prone amplification of the sequences and cyclic repeating of the process. The SELEX procedure includes successive steps consisting of selection (binding, partition, and elution), amplification and conditioning.

Since each of these processes are possible in a purely non-biological approach, the overall process is rapid and scalable. Specifically, the randomly polymerized library of CNA polymers is exposed to the target compounds (for example, the SELEX like process is used to detect an active pharmaceutical agent from the small molecule group and oligonucleotides from the large molecule group as indicated in the) in a column format. Those random sequences with greater affinity for the target will remain in the column longer, and are isolated, e.g. those sequences with the highest affinity are isolated.

Figure 4:
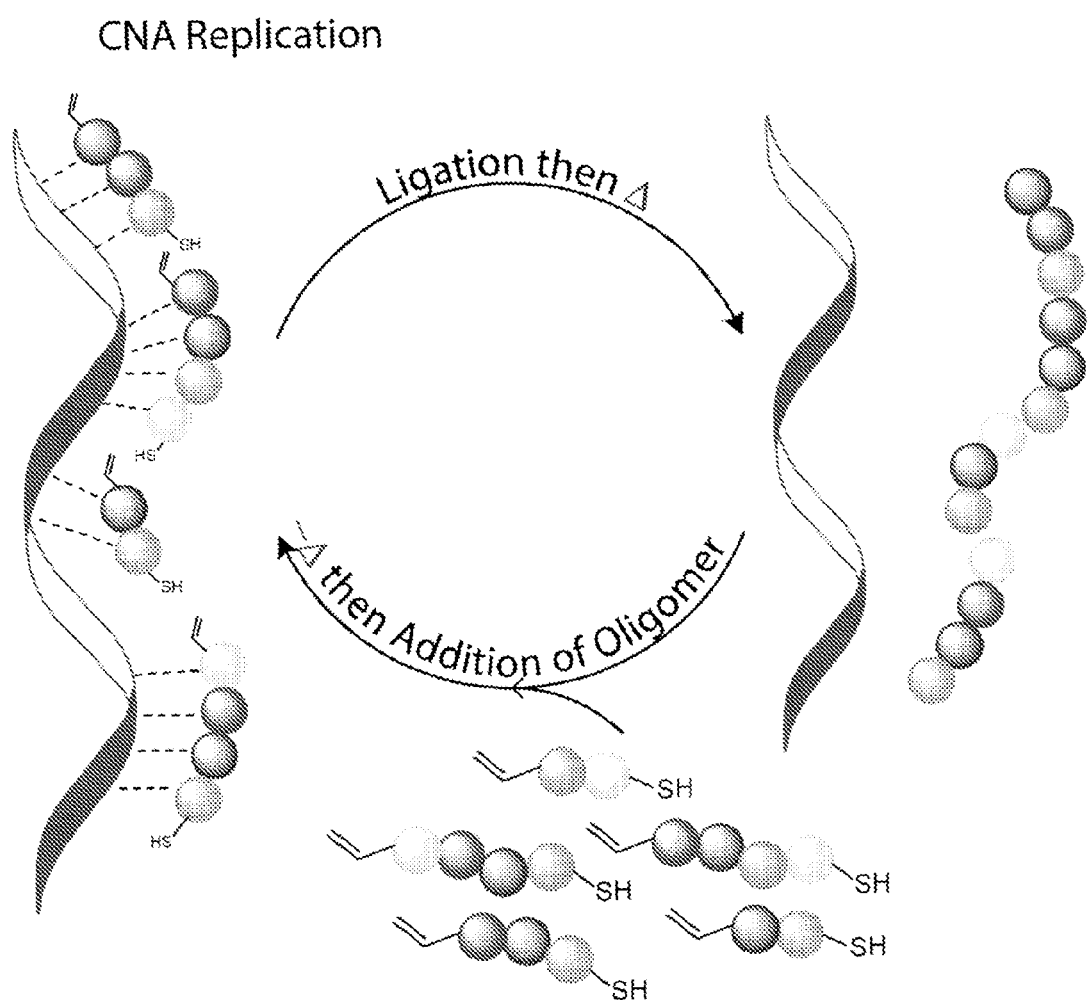
FIG. 4 is a simplified illustration of target specific CNA selection and amplification through a modified SELEX process.

Subsequently, as shown in FIG. 4, the sequences of the isolated molecules are amplified in a PCR-like doubling process (though one that is purely chemical using the click reaction) the affine sequences, using each of the affine sequences as a template for assembly of the next generation of molecules. By controlling the catalyst concentrations, temperature, initial oligomer feed concentrations, and other conditions, the affine sequences with be replicated with varying error rates to create similar but distinct sequences. Subsequent affinity-amplification cycles will continue to refine the sequences to enhance the specificity and strength of binding. Finally, after a sufficient number of cycles to assure appropriate binding and selectivity, the resulting CNA sequences are isolated and sequenced.

For sequencing the resulting polymers, tunneling spectroscopy is used where each repeat unit in the CNA (or eventually TEZ) is "electronically imaged" and exhibits a resulting electronic structure which is identified as a unique electronic fingerprint. This approach represents a paradigm shift from the current state-of-the-art biomolecule detection and sequencing methods that is ideally suited for the proposed production of non-biological molecules. To demonstrated proof-of-concept capability for this transformative and inherently nanoscaled quantum sequencing technique, which combines concepts from quantum mechanics, nanoscience, and biochemistry to develop unique electronic fingerprints for single biomolecules, individual repeat units and nucleic acids. Quantum mechanical tunneling of positive and negative charges from a sharp metallic tip to single molecules/repeat units generates a map of electronic states of the biomolecules, which was found to be unique for different nucleic acids, including those used in the development of the initial CNA oligomers. For CAN based aptamers, identified unique electronic signatures of CNA oligonucleic acids have been identified, for facile detection and sequencing. These electronic signatures differ not only among the CNA units but also sufficiently from their corresponding DNA counterparts to enable simultaneous detection of aptamers or hybrids comprising both DNA and CNA molecules.

Example 3

Synthesis of Monomers and Libraries

A library of water soluble polymeric compounds based on the CNA approach that includes the four natural nucleobases attached to each of two different backbones, one enabling radical thiol-ene coupling reactions and one enabling thiol-Michael addition reactions. The libraries will consist of the random formation of all polymer sequences with an average of at least 30 repeat units, giving rise to two libraries with at least 1012-1018 molecules from which an appropriate polymer will ultimately be selected. At least three additional libraries of compounds are also designed—one in which the thiol-X backbone is altered to achieve additional chemical structural variation in both stiffness and charge density, one in which non-natural nucleobases are included in the monomer selection, and one in which we seek to develop analogues to peptides rather than oligonucleotides (i.e., the TEZ systems). In the first option period, we will synthesize the monomers and the additional three libraries of compounds that were designed in the base period while optimizing the initial two libraries. In the second option period, we will determine which libraries are most effective for binding each of the target molecules as well as for inducing catalytic function or enabling a response/readout (e.g., a color change or fluorescence).

Example 4

Non-Enzymatic Primer Extension and DNA Templated Polymerization

Enzyme-free copying of DNA sequence is of significant current interest because this can be achieved without the use of very expensive polymerase enzymes (and also very tedious to obtain and select), and can be synthesized in larger scales with different backbones.[v]

The basis of these methods are, a) Watson-Crick recognition and hybridization of the template strand by very short sequences of the polymerizing subunits, b) arrangement of the reactive ends in close proximity on the template, c) conjugation of them by a very efficient reaction. The major reactions used for this purpose in literature are reductive amination, amide formation, native chemical ligation etc. Thiol-ene and thio-Michael reactions are highly proficient class of reactions that can be carried out in a variety of atmospheres.

Figure 11:
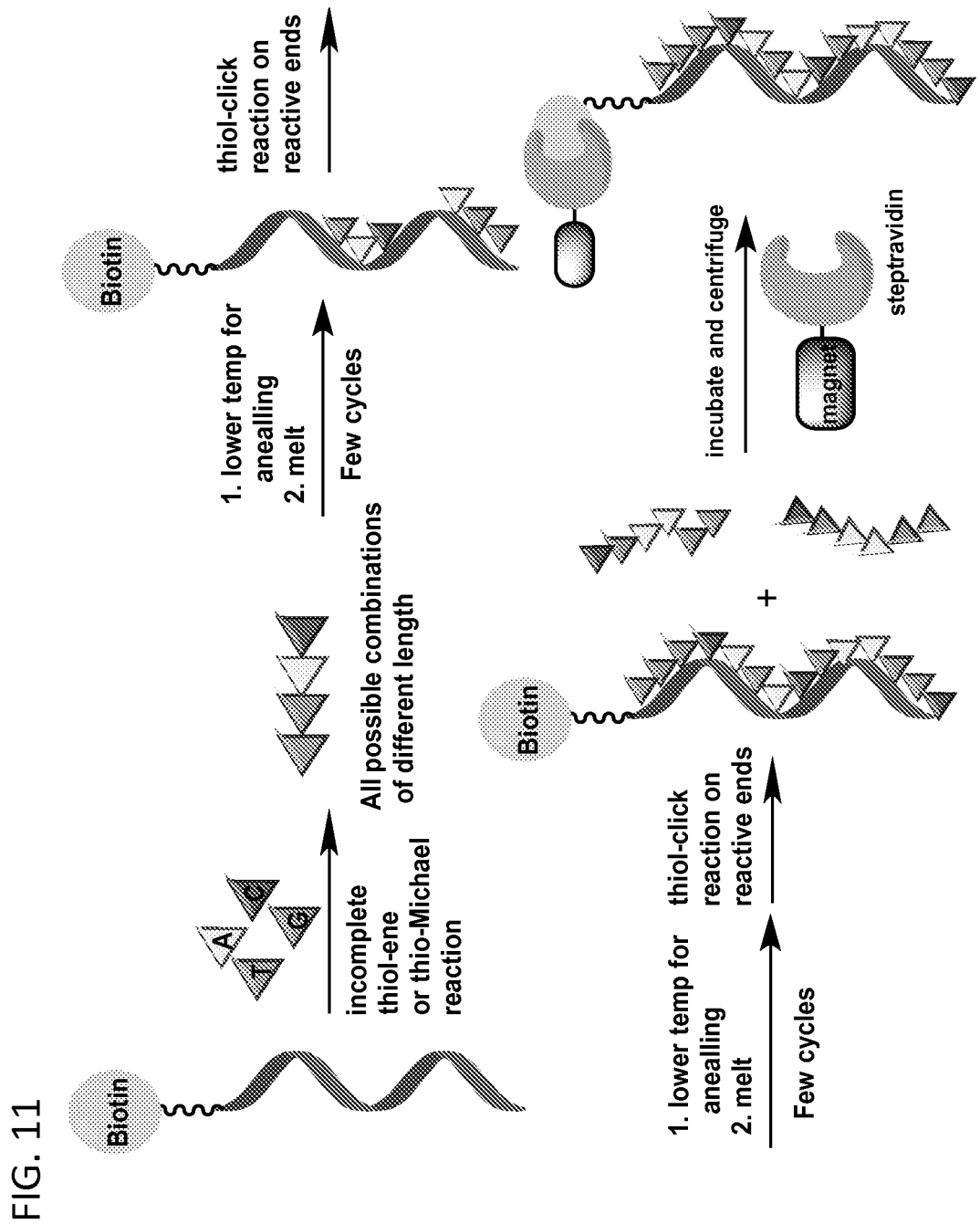
FIG. 11 is a schematic showing a strategy for non-enzymatic CNA primer extension on DNA template.

DNA templated CNA homopolymers synthesis has been demonstrated previously. Therefor sequence defined CNA oligomers are synthesized on a DNA template. Strategically, different type of thiol-ene monomers (both monofunctional and difunctional) are reacted in controlled manner to synthesize a library of shorter oligounits having diverse length and sequence. These are reacted to get longer sequences with subsequent annealing and melting steps in each time to ensure error free template recognition. Finally, the still remaining reactive ends are stitched together on the DNA template by thiol-based click reaction to get the CNA oligomer with complementary sequences (FIG. 11). For purification purpose, the DNA template would be bound to biotin-avidine magnetic beads and after the templated synthesis the daughter oligo can be purified in convenience. Thus specific aims of this strategy are:

a) Synthesis of monofunctional (one thiol and one ene in each end) and difunctional (either two enes in both ends or two thiols) monomer units.
b) Synthesis of reactive-end shorter random sequences in presence or absence of DNA template, hybridization with template and completion of the oligomerization.
c) Purification and characterization of the generated oligomer.

Example 5

CNA Block Copolymers

DNA-block copolymers are hybrid materials of DNA and polymers that have found their applications in biotechnology (e.g. antisense/drug delivery, tissue engineering, DNA vaccination) and nanotechnology (diagnostic device, biosensors, nanoelectronics) and in many others because of their micellar supramolecular structure and ability to encapsulate small molecules inside the hydrophobic core. However, it is difficult to obtain DNA in large scale and as the DNA-polymer coupling is generally performed in aqueous solutions, because of solubility issue, only narrow set of water-soluble polymers remain accessible. Although solid phase methodologies have significantly eliminated the problem, scaling up of such block copolymers is still problematic. Amphiphilic properties of such kind of hybrid materials can be tuned by appropriate selection of DNA sequence and polymer counterparts.

By the synergic combination of thiol-ene or thio-Michael click chemistry and oligonucleotide synthesis, CNA oligomers and polymers can be synthesized in variety of homo-, mixed- and sequence-defined sequences in larger scale, avoiding the complex DNA synthesis chemistry. We propose to create a series of CNA-block copolymers with the combination of different base-sequenced CNA and one or more polymer domains including polyethylene glycol etc. The thio-ether backbone also will impart certain lipophilic character to the oligonucleotide counterpart of the block-copolymer with higher degrees of base-pairing capacities and thus can evolve completely new properties. Additionally, because of the high efficiency of thiol-click reactions, the conjugation can be fabricated even in solid phase and with the ease of photo control. The properties can further be modulated by site-specific hybridization with the CNA domain. Broadly, we propose to create a new type of oligonucleotide-based copolymers with next-gen properties. The broad aims are:

a) Generation of CNA homo- and mixed-base polymers with reactive ends and copolymers formations with PEG, PPO etc. The polymerization can be achieved by polymerization from end or by stitching CNA and individual polymer blocks together by thiol-ene chemistry. A variety of diblock and triblock copolymers will be attempted to obtain A-B, A-B-A and A-B-C kind of block copolymers.

b) Application of those BCPs in surface patterning.

c) Synthesis of CNA-polyarginine/polylysine copolymers for cellular delivery and antibiotic applications.

d) Use of CNA-copolymers as dispersion, stabilization and size-selection agent for single-wall carbon nanotubes (SWNT).

We claim:

1. A thiol-X clickable monomer having the formula:

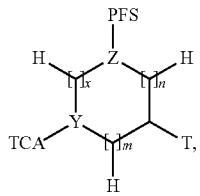

wherein Y and Z are each independently carbon or nitrogen;
n is an integer from 0-10;
m is an integer from 0-10;
x is an integer from 0-10;
PFS has the formula:

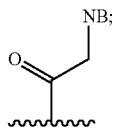

NB is a nucleobase;
T is a thiol having the formula:

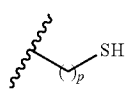

p is an integer from 0 to 4; and
TCA is a thiol-click acceptor.

2. The thiol-X clickable monomer according to claim 1, wherein the thiol-X clickable monomer has the formula:

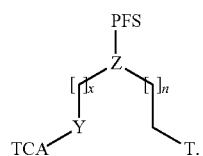

3. The thiol-X clickable monomer according to claim 2, wherein the monomer is a 6-atom unit that includes the carbon atom to which the thiol moiety of the TCA thiol-click acceptor is bonded thereto.

4. The thiol-X clickable monomer according to claim 2, wherein Y is carbon and Z is nitrogen.

5. The thiol-X clickable monomer according to claim 2, wherein the thiol-click acceptor comprises a vinyl, vinyl ether, allyl ether, norbornene, vinyl sulfone, epoxy, acrylate, isocyanate, alkyne, methacrylate, maleimide, halide or alkyl extensions thereof.

6. The thiol-X clickable monomer according to claim 5, wherein the vinyl moiety has the formula:

—$CR_5$=$CR_6R_7$, wherein $R_5$, $R_6$, and $R_7$ are independently hydrogen, hydrocarbyl, substituted hydrocarbyl, substituted heterocyclo, alkyl, substituted alkyl, acyl, —C(O)R, —C(O)OR, or —C(O)$NR_aR_b$, substituted or unsubstituted aryl or a heterocyclic ring; R is hydrocarbyl, substituted hydrocarbyl or heterocyclo, $R_a$ and $R_b$ are independently hydrogen, hydrocarbyl, substituted hydrocarbyl or heterocyclo.

7. The thiol-X clickable monomer according to claim 1, wherein the index n is 0 and the index p is 1.

8. The thiol-X clickable monomer according to claim 1, wherein the thiol-click acceptor is chosen from:

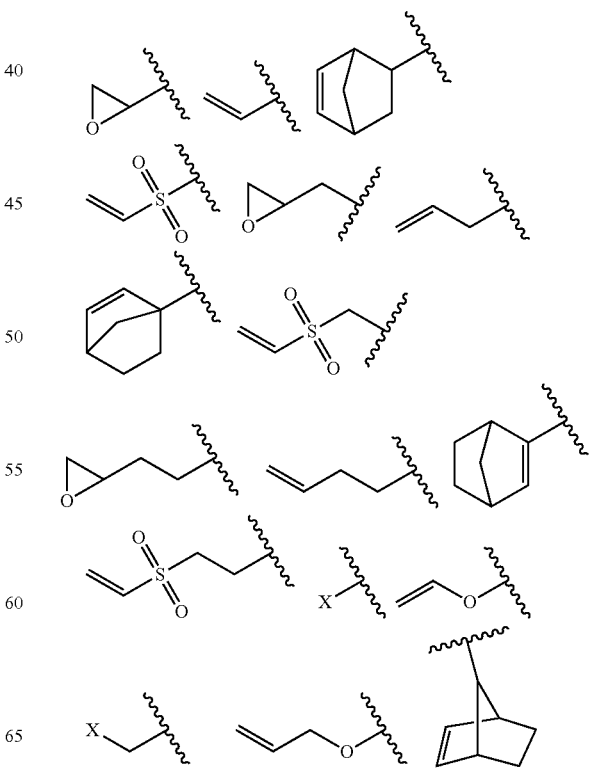

-continued

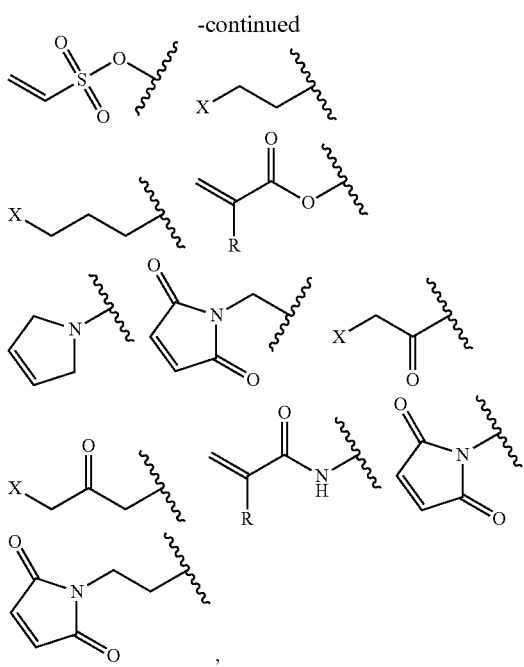

where X is a halide and R is a hydrogen or alkyl chain.

9. The thiol-X clickable monomer according to claim 1, wherein nucleobase has the formula:

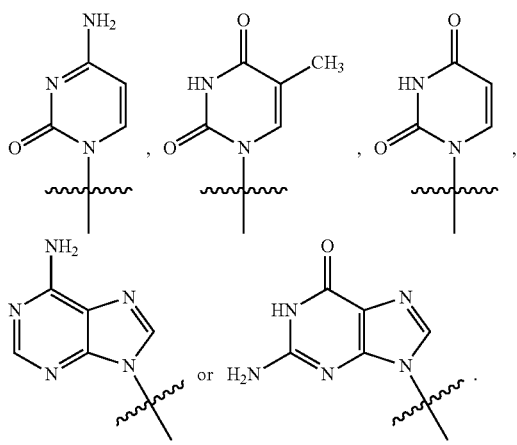

10. A click nucleic acid polymer having the formula:

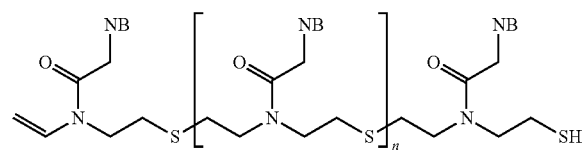

wherein NB is a nucleobase, and the index n is from 4 to about 500.

11. The polymer according to claim 10, wherein the nucleobase is chosen from 5-fluorouracil, 5-bromouracil, 5-chlorouracil, 5-iodouracil, hypoxanthine, xanthine, acetyl-cytosine, 5-(carboxyhydroxylmethyl) uracil, 5-carboxymethylaminomethyl-2-thiouridine, 5-carboxymethylaminomethyluracil, dihydrouracil, beta-D-galactosyl-queosine, inosine, N6-isopentenyladenine, 1-methylguanine, 1-methylinosine, 2,2-dimethylguanine, 2-methyladenine, 2-methylguanine, 3-methylcytosine, 5-methyl-cytosine, N6-adenine, 7-methylguanine, 5-methylaminomethyluracil, methoxyamino-methyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudo-uracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N2-carboxypropyl) uracil, and 2,6-diaminopurine.

12. The polymer according to claim 10, wherein the nucleobase has the formula:

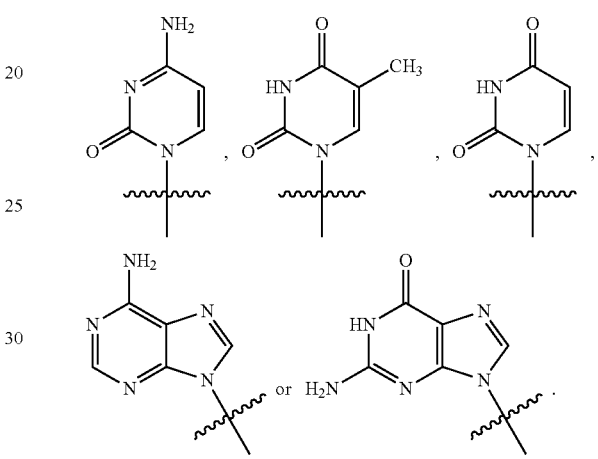

13. The polymer according to claim 10, wherein n is from 18 to 30.

14. A composition, comprising a thiol-X clickable monomer having the formula:

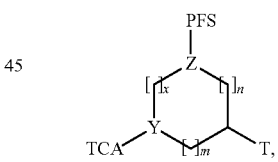

wherein Y and Z are each independently carbon or nitrogen;

n is an integer from 0-10;

m is an integer from 0-10;

x is an integer from 0-10;

PFS has the formula:

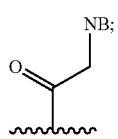

NB is a nucleobase;

T is a thiol having the formula:

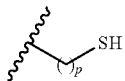

p is an integer from 0 to 4; and
TCA is a thiol-click acceptor.

15. The composition according to claim 14, wherein the thiol-X clickable monomer has the formula:

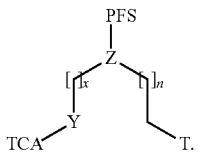

16. The composition according to claim 15, wherein the monomer is a 6-atom unit that includes the carbon atom to which the thiol moiety of the TCA thiol-click acceptor is bonded thereto.

17. The composition according to claim 15, wherein Y is carbon and Z is nitrogen.

18. The composition according to claim 14, further comprising a pharmaceutically acceptable carrier.

19. The composition according to claim 14, wherein the nucleobase is chosen from 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosyl-queosine, inosine, N6-isopentenyladenine, 1-methylguanine, 1-methylinosine, 2,2-dimethylguanine, 2-methyladenine, 2-methylguanine, 3-methylcytosine, 5-methyl-cytosine, N6-adenine, 7-methylguanine, 5-methylaminomethyluracil, methoxyamino-methyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudo-uracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N2-carboxypropyl) uracil, and 2,6-diaminopurine.

20. The composition according to claim 14, wherein the nucleobase has the formula:

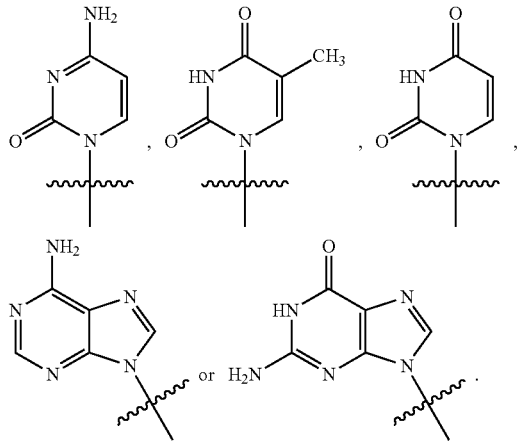

* * * * *